United States Patent [19]
Taylor, Jr.

[11] Patent Number: 6,160,481
[45] Date of Patent: Dec. 12, 2000

[54] MONITORING SYSTEM

[76] Inventor: John E Taylor, Jr., 19080 SW. 44th St., Dunnellon, Fla. 34432

[21] Appl. No.: 09/229,023

[22] Filed: Jan. 12, 1999

Related U.S. Application Data

[63] Continuation-in-part of application No. 08/926,746, Sep. 10, 1997, Pat. No. 5,867,103.

[51] Int. Cl.[7] .................................................. G08B 21/02
[52] U.S. Cl. ......................... 340/573.4; 340/539; 379/38
[58] Field of Search ............................ 340/573.4, 573.1, 340/539; 379/38

[56] References Cited

U.S. PATENT DOCUMENTS

| | | | |
|---|---|---|---|
| 5,461,390 | 10/1995 | Hoshen | 340/573.4 |
| 5,990,793 | 11/1999 | Bieback | 340/573.1 |
| 6,054,928 | 4/2000 | Lemelson et al. | 340/573.4 |

*Primary Examiner*—Glenn Swann

[57] ABSTRACT

A monitoring system provides for monitoring of a person and taking an action to dissuade the person from a course of action. The system has a device attached to the person which includes mechanisms to provide for an intervention to dissuade the person from the course of action. The intervention may be in the form of delivery of either a medication or an electrical shock to the person. The system may further include monitoring of a bodily function of the person or positional tracking of the person. Various scenarios are described to provide for activation of the intervention. The system may include a second device in possession of a restrictor person with positional tracking of this person and comparison relative to the positional location of a restrictee person.

19 Claims, 12 Drawing Sheets

MONITORING SYSTEM

CROSS-REFERENCE

This application is a continuation-in-part of Ser. No.: 08/926,746 filed Sep. 10, 1997, entitled "Monitored Person Tracking System", now U.S. Pat. No. 5,867,103. The original application is incorporated herein by this reference.

BACKGROUND

1. Field of the Invention

Generally, the invention relates to monitoring of persons. More specifically, the invention relates to such monitoring wherein at least one monitored person has a portable monitoring device attached thereto.

2. Description of the Prior Art

Our society has been compelled to confine individuals as a result of their behavior which has been deemed unacceptable to the best interest of society. Historically, such confinement has occurred at centralized locations where numerous confinements occur simultaneously. It is expensive for society to maintain such centralized locations due primarily to construction cost, upkeep cost, supervisory personnel expense and medical care for the persons being confined. These persons being confined represent both those convicted of committing a crime as well as those accused of committing a crime, but awaiting trial.

Our society has begun to seek alternative means of confining those individuals convicted of committing a crime or accused of committing a crime while awaiting trial where those individuals are deemed to be non-violent. Parole, probation and house arrest programs have existed for some time and are being extensively utilized by the justice system for certain type of crimes.

Additionally, our society has recently made progress toward restricting the activities of certain habitual offenders of certain type of crimes even following completion of court appointed sentences. These restrictions are coming in the form of civil actions as compared to criminal actions. Some circumstances require continued conventional confinement while others require site confinement or other monitoring of activities. Examples of such crimes include child molestation and other sex crimes.

People produce certain bodily signals which may be detected and measured by equipment. Examples of these bodily signals include blood pressure, heart beat rate, respiration rate, body temperature, blood oxygen level and blood alcohol level. Such bodily signals may be measured to determine a specific base line measurement for a respective person. Such base line measurements may then be redefined, if desired, on a periodic basis. Certain bodily functions, and therefore measurements taken thereof, vary depending upon the activity engaged in at the time of measurement. Therefore, such measurements will involuntarily change when the individual is engaging in activities which are generally prohibited to the population or specifically prohibited to the individual. The mere fact that a specific individual is aware that monitoring is occurring will tend to dissuade the individual from engaging in prohibited behavior.

Referring now specifically to site confinement, a common type of monitoring system, it is conventionally known to provide for such site confinement of individuals wherein means are provided within the respective system to indicate that a respective individual has violated boundaries of their respective site. Several of these systems include means to detect tampering with various elements of the system.

The most common type of such a site confinement system comprises three devices being a central processing unit, at least one transportable device and at least one base unit. The transportable device, which securely attaches to the individual being confined, comprises communication means to communicate with the base unit. The base unit, which is positioned within the boundaries of the confinement site, comprises two types of communication means. The first of the communication means allows the base unit to communicate with the transportable device. The second of the communication means allows the base unit to communicate with the central processing unit. Generally, this communication is over a ground based telephone system. When communication is not present between the transportable device and the base unit, the base unit, utilizing the second communication means, communicates with the central processing unit to notify an oversight authority of a possible violation of the confinement by the individual. As can readily be seen such systems have a general deficiency in that they are bound to a single designated site location. Several systems have been proposed which allow for a wider tracking of individuals.

As can be seen various attempts have been made to provide for a method of restricting the activities of certain individuals. These attempts have been less efficient than desired. As such, it may be appreciated that there continues to be a need for a system which may monitor at least one individual without relying upon limitations associated with site boundaries. The present invention substantially fulfills these needs.

SUMMARY

In view of the foregoing disadvantages inherent in the known types of monitoring systems, your applicant has devised a system which provides for monitoring of a plurality of monitored persons. A first embodiment of a system has a portable monitoring device for each of the monitored persons, means to acquire a transmission, means to create a bodily signal reference indicative of a physiological sign of the monitored person and means to store within a database a series of the bodily signal references. Each of the portable monitoring devices further has means to provide for attachment to the respective monitored person, means for detecting a bodily signal produced by the monitored person and means for transmitting a signal. A second embodiment of a system has a portable monitoring device for each of the monitored persons, means to acquire a transmission, means to determine a status of a respective portable monitoring device, a conditional database, means to compare a status of the respective portable monitoring device and means to activate an intervention. Each of the portable monitoring devices further has means to provide for secure attachment to the respective monitored person, means to detect tampering with the portable monitoring device, means to receive a distinct signal, means for transmitting a signal and means to intervene mechanically.

My invention resides not in any one of these features per se, but rather in the particular combinations of them herein disclosed and it is distinguished from the prior art in these particular combinations of these structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore a primary object of the present invention to provide for a portable monitoring of individuals.

Other objects include;

a) to provide for a portable monitoring device which may be secured to a monitored person.

b) to provide for detecting tampering with the portable monitoring device.

c) to provide for a transfer of a signal from the portable monitoring device.

d) to provide for a receipt of the signal transferred by the portable monitoring device.

e) to provide for determining a position reference of a positional location of the portable monitoring device based upon at least one signal received by the portable monitoring device wherein the signal is generated by at least one detached sending unit.

f) to provide for monitoring of a bodily signal produced by the monitored person.

g) to provide for a notification to a central location, such as nursing station or other health monitoring agency, of any indication of a possible medical emergency of the monitored person when physiological readings are outside of range from a baseline reading for the respective monitored person.

h) to provide for a medical monitoring of individuals who may require the need of emergency personnel which may be done on an automatic basis once the physiological monitored signs of the monitored person indicates levels outside of a desired range for the individual where the notification may take place automatically by notifying the proper emergency personnel of the individuals condition and location.

i) to provide for notification of on site supervisory personnel when a monitored person is a resident of a facility such as a retirement home, hospital, nursing home, prison amongst others, when physiological readings for the monitored person are outside of an acceptable range for the monitored person where the notification include the physiological readings and/or a physical location of the monitored person.

j) to provide for medical monitoring of Alzheimers, mentally ill, elderly individuals on a round the clock basis.

k) to provide for an active response through a digital readout directly to the monitored person to provide instructions or commands to the monitored person in response to a variation in a bodily signal measurement beyond a predetermined range.

l) to provide for a mechanical intervention to physically dissuade the monitored person from a specific course of action.

m) to provide for generating an associated occurrence reference indicative of a time span related to a position reference and/or a bodily signal reference.

n) to provide for a storage of at least a series of position references and/or bodily signal references along with associated occurrence references within a database.

o) to provide for deterring crime by providing the monitored person with a knowledge of the monitoring of the bodily signal.

p) to provide for deterring crime by providing the monitored person with a knowledge of the possibility of activation of the mechanical intervention in response to an unacceptable specific course of action.

q) to provide for at least a pair of portable monitoring devices which each transfer position references for comparison to determine if any select pair of the portable monitoring devices are within a predetermined distance measurement of each other.

r) to provide for a notification if any select pair of portable monitoring devices are within the predetermined distance measurement of each other.

s) to provide for a secondary transportable device capable of communicating with a respective portable monitoring device, where the portable monitoring device is secured to a respective monitored person, wherein at least some function is performed by the secondary transportable device to reduce an overall weight of the portable monitoring device secured to the monitored person.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated the preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION

Figure 1:
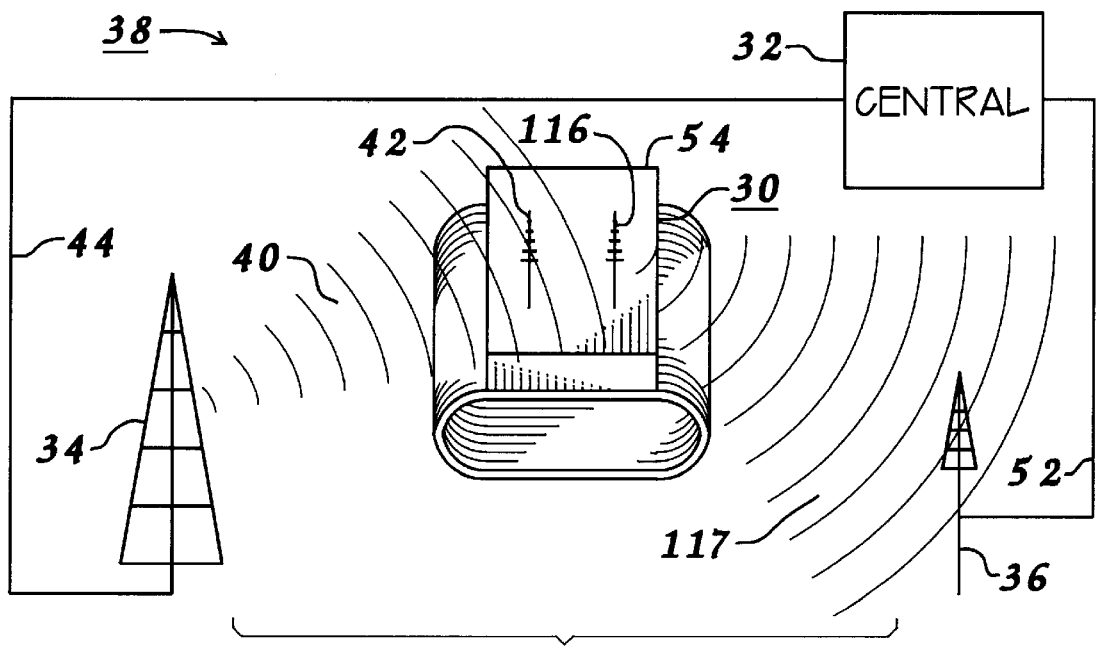
FIG. 1 is a an illustration of an embodiment of a monitoring system.

Many different systems having features of the present invention are possible. The following description describes the preferred embodiment of select features of those systems and various combinations thereof. These features may be deployed in various combinations to arrive at various desired working configurations of systems.

Referring is hereafter made to the drawings where like reference numerals refer to like parts throughout the various views.

FIG. 1 depicts a portable monitoring device 30, a central location 32, a transmission tower 34 and a receiving tower 36 forming a monitoring system 38.

Central Location

It is a requirement of the present invention that a central location, or locations, be provided which will receive communication from and/or send communication to at least select deployed components of any specific deployed system. This communication will be specific to the overall configuration of the specific deployed system. Generally, the central location will; receive communication from deployed components and/or send communication to deployed components and/or store information and/or perform computational calculations on information and/or allow access to information by supervisory personnel. While the central location may be dedicated to a monitoring of a system of the present invention it is possible that the central location may be non-dedicated, or have a primary purpose other than monitoring the system of the present invention. Examples of such non-dedicated central locations include public and private institutions such as police stations, fire department stations, existing burglar alarm monitoring locations, hospitals, retirement homes, nursing homes or schools.

FIG. 1 depicts central location 32 housing various equipment, more fully described elsewhere herein, of monitoring system 38 having features of the present invention. Supervisory personnel, not shown, would have access to exert control over, or otherwise interface with, monitoring system 38 at central location 32.

Detached Sending Units

In certain deployments it is a requirement that a method exist to provide for making a determination of a location of at least select members of the portable monitoring devices attached to respective monitored persons. To this end, a signal, or signals, must be produced by at least one detached sending unit. This signal, or signals, is subsequently received by at least one other component of the system wherein an eventuation is made to provide for a determination of the location of a respective portable monitoring device attached to a respective monitored person. The detached sending units may be fixed ground based, moveable ground based, orbital or a combination thereof.

FIG. 1 depicts transmission tower 34, being an example of a detached sending unit, and capable of broadcasting a signal 40 for subsequent reception by a reception antenna 42 of portable monitoring device 30. Transmission tower 34 may receive a signal from central location 32 through a coupling 44 which is broadcast by transmission tower 34 as signal 40.

Figure 4:
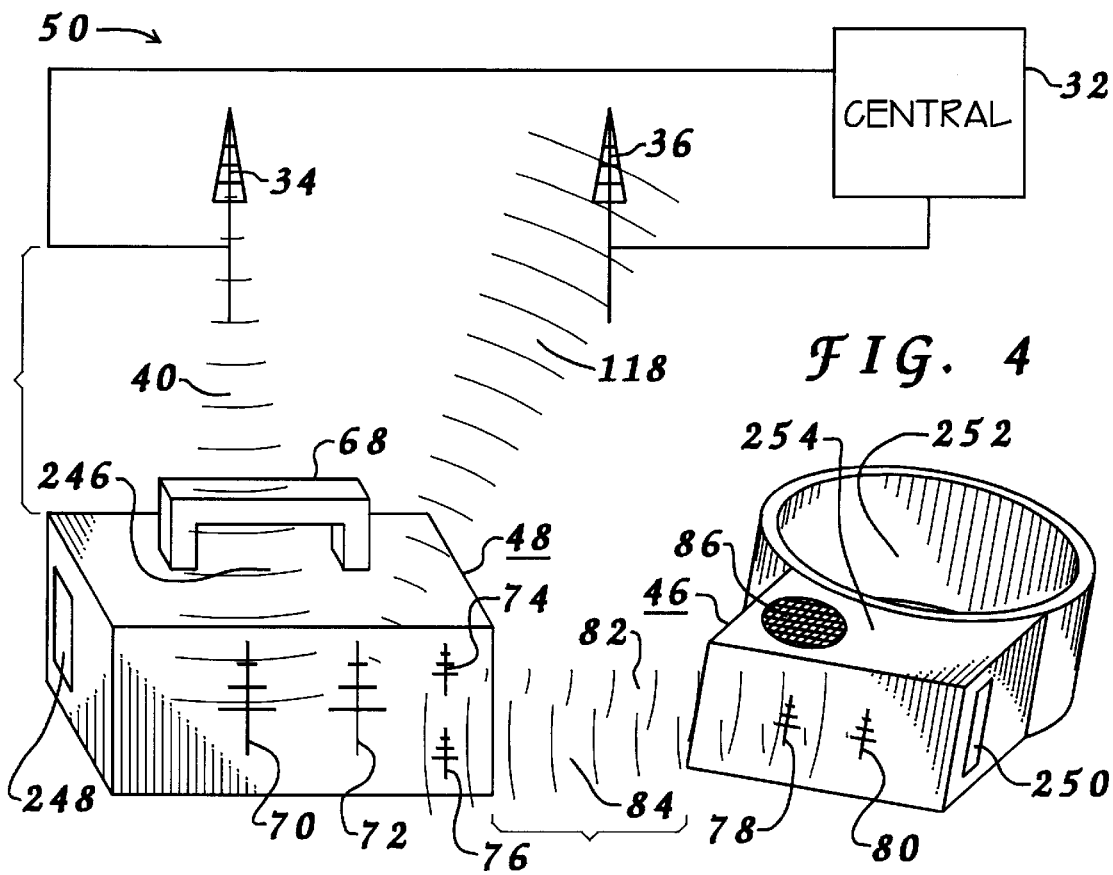
FIG. 4 is an illustration of another embodiment of the monitoring system.

FIG. 4 depicts central location 32, transmission tower 34, a portable monitoring device 46, a secondary transportable device 48 and receiving tower 36 forming a monitoring system 50. In this embodiment, both secondary transportable device 48 and transmission tower 34 are considered to be detached sending units.

Relay Equipment

It is a requirement that the central location(s) be capable of communicating with respective portable monitoring devices. This communication may be either from the central location to respective portable monitoring devices, from respective portable monitoring devices to the central location or both. Preferably, such communication involves wireless communication utilizing either a ground based system or an orbital system or both. Many such systems are conventionally known in the art and many of these systems may be utilized for the present invention. Additionally, for the sake of economics, it is desirable to have such communication transfers utilize, at least partially, existing ground based communication systems as exampled by phone lines.

FIG. 1 depicts coupling 44 transferring a signal from central location 32 to transmission tower 34. FIG. 1 also depicts a coupling 52 transferring a signal from receiving tower 36 to central location 32. Couplings 44 and 52 represent conventional ground based communication systems, conventional wireless communication systems or a combination of both.

Portable Monitoring Device

It is a requirement of the present invention that a portable monitoring device be provided for each monitored person. It is a strong desire that the portable monitoring device comprise; means to attach the portable monitoring device to the monitored person and control means. In certain deployments the portable monitoring device will further comprises additional features in various combinations. Three of these features comprise; means to detect tampering with the portable monitoring device, means to receive a signal and means to send a signal.

Alternatively, it is possible to provide for a combination of a portable monitoring device as defined above and a secondary transportable device. In such a combination certain functions may be performed by the secondary transportable device thus eliminating the requirement of providing structures on or in the portable monitoring device to perform those functions. This provides for a reduction in the required weight of the portable monitoring device, which must be attached to the monitored person, without loss of the otherwise desired function. One example of such a combination provides for structures to provide for short range communication between the portable monitoring device and the secondary transportable device while providing bulkier structures on the secondary transportable device to provide for transmission of a signal for eventual transfer to the central location.

The art is rich with similar devices, and combinations of devices, for usage within various systems, as exampled by those systems designed to provide for site confinement of individuals. Many of these devices conventionally known in the art may be modified to be employed for the present invention.

The means to secure may involve surrounding engagement of a portion of the body of the monitored person or may involve implantation. The preferred method of securement is the surrounding engagement method. The most obvious attachment locations for such attachment being around a wrist, around an arm, around an ankle, around a leg, around the chest, around the waist or around the neck. Implantation is possible, though less desirable due to power supply requirements.

Figure 2:
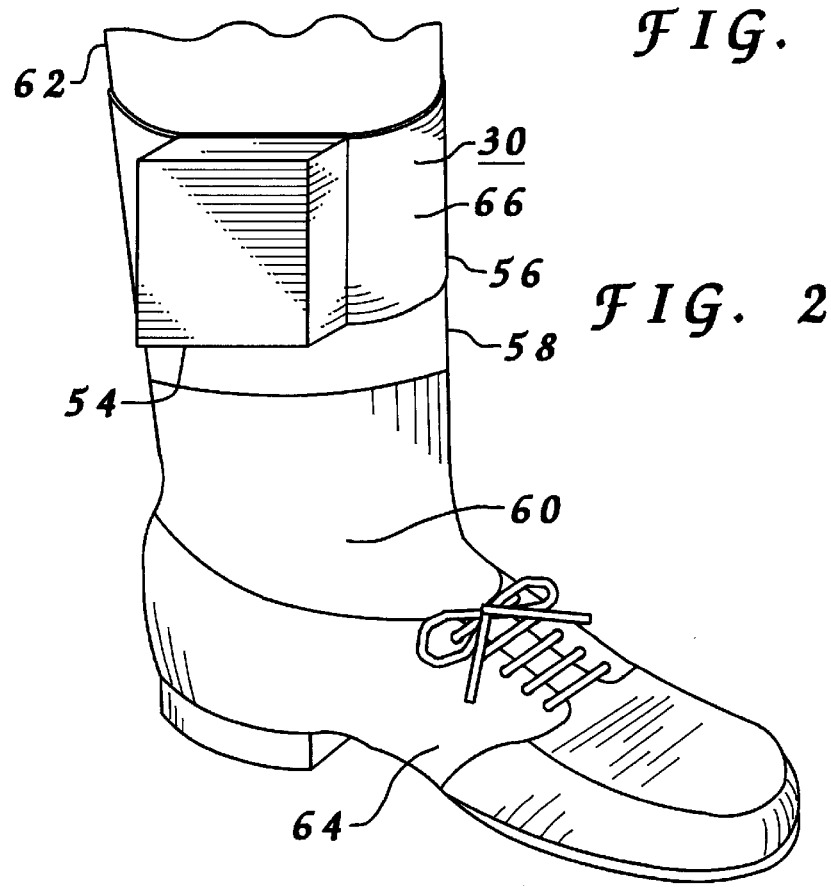
FIG. 2 is a perspective view of a portable monitoring device attached to a monitored person.

FIG. 1 and FIG. 2 depict portable monitoring device 30 which comprises a housing 54 and a band 56. Band 56 surrounds a leg 58, at an ankle 60, and locks to housing 54 to secure portable monitoring device 30 to a monitored person 62, see FIG. 2. Band 56 is adjusted to be of a sufficient length that portable monitoring device 30 will not move past a foot 64, see FIG. 2.

The means to detect tampering, where the securing means involve surrounding engagement of a portion of the body of the monitored person, will require that the surrounding band retain its prior integrity. This will involve means to ensure that the surrounding band is intact and, if connected to a housing, that such connections are intact. Without regard for the specific securing means employed, it is a strong desire that means be provided to detect any tampering with the housing containing the equipment.

FIG. 2 depicts band 56 having a severing detection device 66 contained therein. Severing detection device 66, contained within band 56, connects, at opposing end thereof, to housing 54. As conventionally known in the art, equipment, not shown, contained in portable monitoring device 30 is capable of determining and reporting if any deviation in power through severing detection device 66 is detected. This prevents bypassing power transfer along severing detection device 66 while allowing for the severing of severing detection device 66. Similar equipment, conventionally known and not shown, allows for a detection of tampering with housing 54 or any other component of portable monitoring device 30.

In certain deployments it is desirable to provide for a stationary device which would cooperate with the portable monitoring device attached to the monitored person. This is particularly desirable where the monitored person is restricted to remain in a stationary location during the period of time of monitoring. Alternatively, in certain deployments it is desirable to provide for a secondary transportable device which would cooperate with the portable monitoring device attached to the monitored person. This is particularly desirable where the monitored person will predominately be in stationary locations for extended periods of time.

Monitoring system 50 has many of the required features as well as many optional features. FIG. 4 depicts monitoring system 50 comprising secondary transportable device 48 and portable monitoring device 46. Portable monitoring device 46 is securable to a monitored person, not shown in this view, and therefore is free moving with the monitored person. Secondary transportable device 48 is shown as being moveable by the monitored person using a handle 68. In this embodiment, or variations thereof, the monitored person would be required to remain within a predetermined communication range from secondary transportable device 48 wherein portable monitoring device 46, attached to the monitored person, and secondary transportable device 48 could communicate. This would allow the monitored person to have a free range zone about secondary transportable device 48 within which the monitored person could move. When the monitored person desires to moves beyond that range the monitored person would be required to move secondary transportable device 48. This arrangement affords the monitored person complete mobility while requiring that a minimum amount of equipment be secured to the monitored person.

Secondary transportable device 48 has a long range reception antenna 70, a long range transmission antenna 72, a short range transmission antenna 74 and a short range reception antenna 76. Portable monitoring device 46 has the previously disclosed securing means and tamper detection means. Additionally, portable monitoring device 46 further comprises a short range reception antenna 78 and a short range transmission antenna 80. Short range transmission antenna 74 of secondary transportable device 48 is capable of broadcasting a signal 82 which is received by short range reception antenna 78 of portable monitoring device 46. Short range transmission antenna 80 of portable monitoring device 46 is capable of broadcasting a signal 84 which is received by short range reception antenna 76 of secondary transportable device 48. This provides for communication between secondary transportable device 48 and portable monitoring device 46 while within the free range zone. Movement beyond this range would result in a lack of communication and result in an indication that the monitored person was in violation of monitoring rules. A warning buzzer 86 would warn the monitored person that this range was being approached when communication still existed, but was determined to be weak. As more fully disclosed below, means may be provided to determine a distance and an orientation of portable monitoring device 46 relative to secondary transportable device 48.

Figure 6:
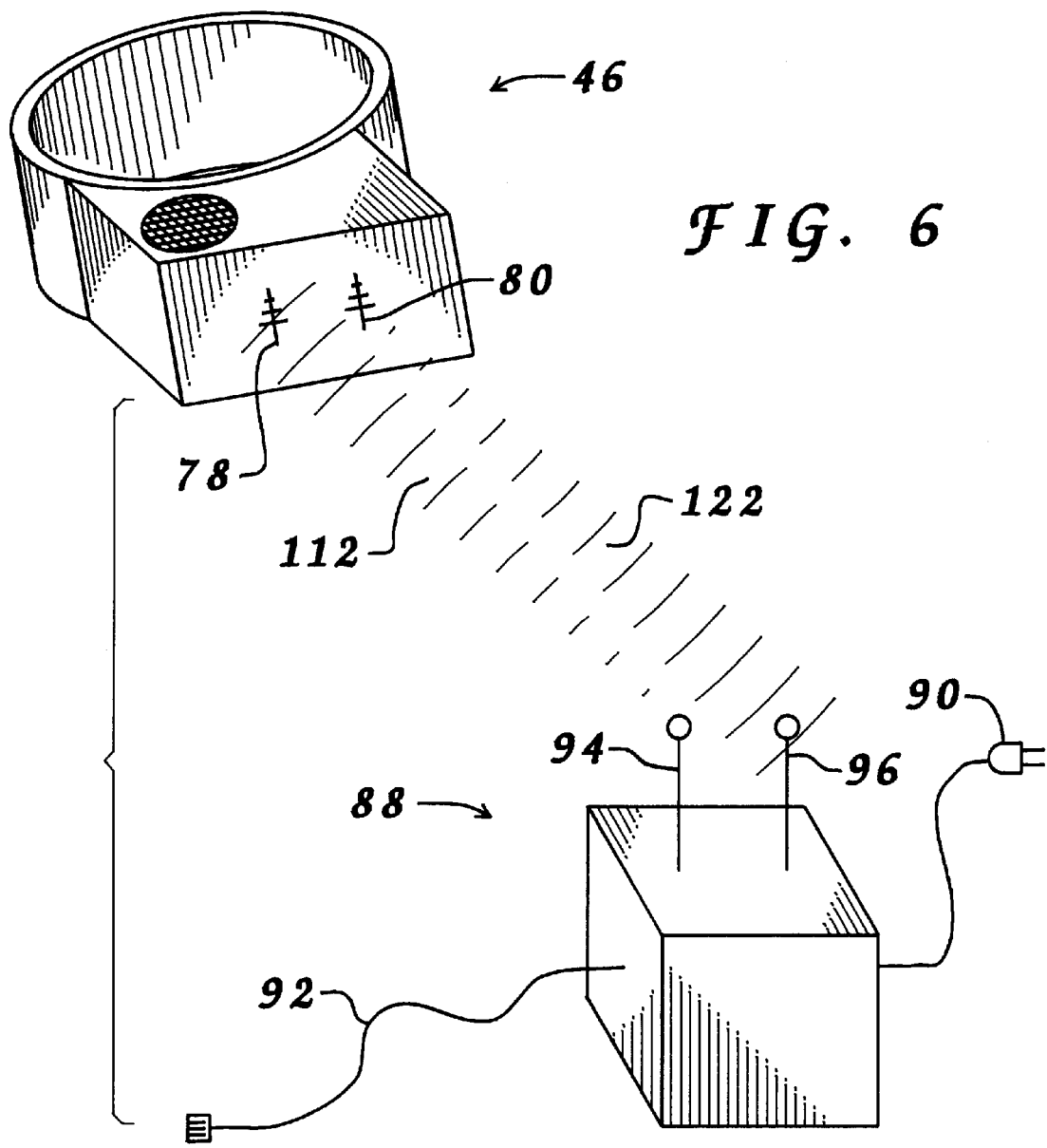
FIG. 6 is a perspective view of another embodiment of the monitoring system.

FIG. 6 depicts a stationary device 88 and portable monitoring device 46, (as depicted in FIG. 4). Stationary device 88 would have a permanent power supply as exampled by connection of a power plug 90 to a standard wall outlet, not shown. Stationary device 88 further comprises a ground based connection to a communication system as exampled by connection of a phone line 92 to a wall jack, not shown. This arrangement provides for ready communication with central location, not shown in this view, while eliminating the requirement of providing a transportable power supply to that equipment contained within and about stationary device 88. Stationary device 88 further comprises a short range transmission antenna 94 and a short range reception antenna 96 to provide for communication with portable monitoring device 46. This arrangement is ideal where the other features of the present invention are desired and where the monitored person is otherwise limited in their mobility.

Transmission Acquisition Means

In certain deployments it is a strong desire that the portable monitoring device further comprise transmission acquisition means to provide for receiving a signal sent by other components of the system. The signal received may be data containing instructions transferred from the central location, or data as exampled by information necessary to permit subsequent calculations to provide for a making of a positional determination.

Numerous methods are conventionally known in the art to acquire signals transmitted by other electronic equipment via ground based communication, via wireless communication or via a combination of ground based and wireless communications. Many of these methods may be employed with the present invention. The signal transmitted by the portable monitoring device may be sent via direct contact with a base unit, indirect contact with a base unit or general wireless broadcast, as more fully described elsewhere herein. Following transmission of the signal by the portable monitoring device it is a desire to acquire that signal at a central location. This acquisition may be directly by the central location or, more likely, will involve intermediate reception by other equipment which then transfers the signal on to the central location. (The term central location is not intended to be limited to one physical location for the tracking system, but rather a location, or locations, where data is gathered from distinct portable monitoring devices.) The means to receive a signal may be performed by various types of equipment conventionally known in the art depending upon the type of signal being received. Many of these methods may be employed with the present invention.

Figure 3:
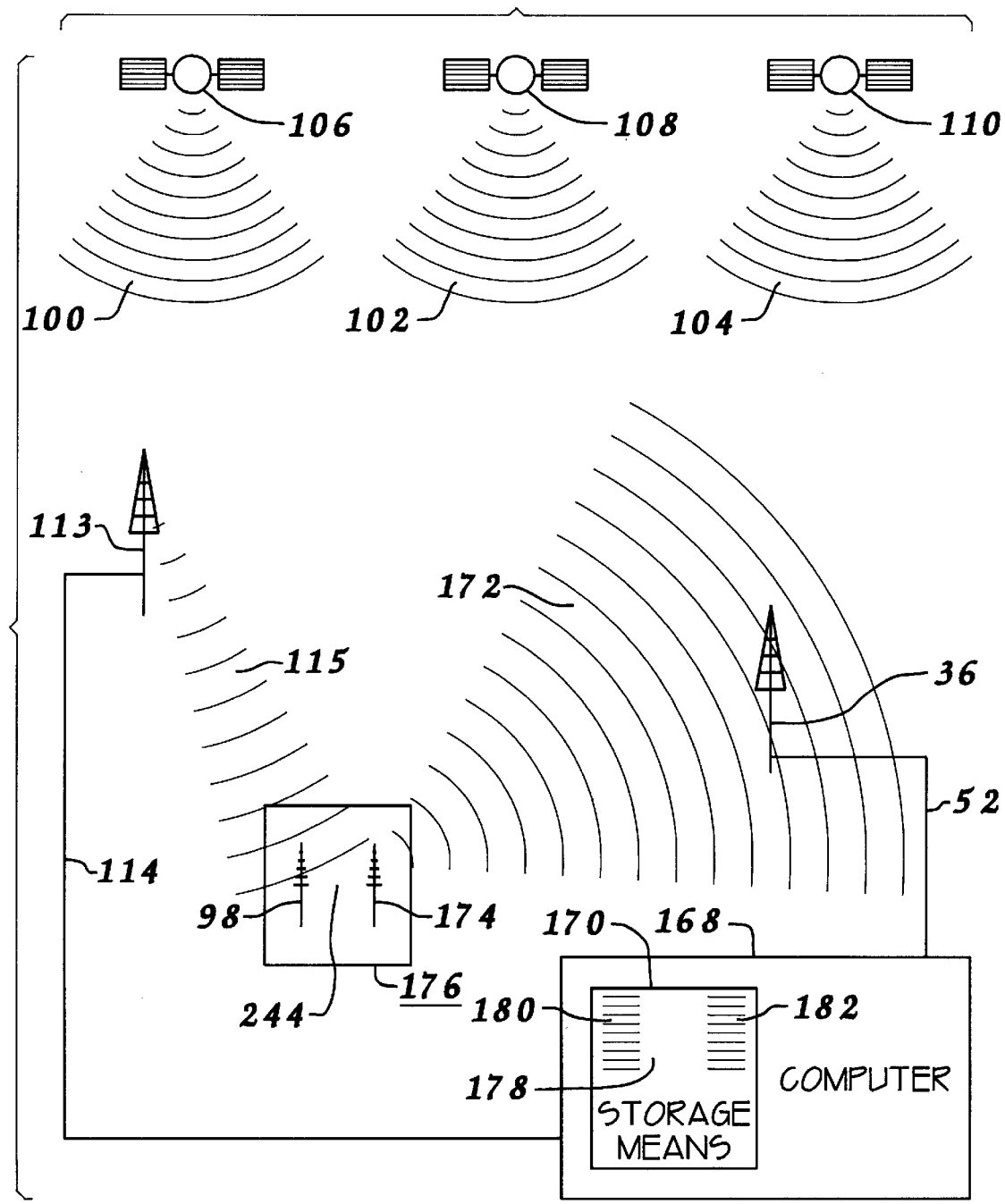
FIG. 3 is an illustration of another embodiment of the monitoring system.

FIG. 1 depicts reception antenna 42 contained within housing 54 of portable monitoring device 30. Reception antenna 42 is capable of receiving signal 40, or signals, as sent by transmission antenna 34, in this example a ground based unit. FIG. 3 depicts a reception antenna 98 capable of receiving signals 100, 102 and 104 from satellites 106, 108 and 110 respectively. Satellites 106, 108 and 110 are further exampled of detached sending units. FIG. 4 depicts long range reception antenna 70 of secondary transportable device 48 capable of receiving signal 40 from transmission tower 34. FIG. 4 also depicts short range reception antenna 78 of portable monitoring device 46 capable of receiving signal 82 from short range transmission antenna 74 of secondary transportable device 48. FIG. 6 depicts phone line 92 of stationary device 88 capable of receiving a signal from other components of the system, not shown in this view. FIG. 6 also depicts short range reception antenna 78 of portable monitoring device 46 capable of receiving a signal 112 from short range transmission antenna 94 of stationary device 88.

FIG. 3 also depicts a transmission tower 113 linked to computer 168 by a coupling 114. Ground based transmission tower 113 is capable of producing a signal 115 for subsequent reception by reception antenna 98 of portable monitoring device 176. When ground produced signal 115 is utilized in conjunction with at least select signals 100, 102 or 104, position reference 244 may be a more precise reference than the precision of the reference obtainable only with space generated signals 100, 102 or 104.

Transmitting Means

In certain deployments it is a strong desire that the portable monitoring device further comprise transmitting means to provide for sending a signal to other components of the system. The signal sent may be data containing information about the monitored person or may be data seeking further instruction from other components of the system.

The means to transmit a signal may involve sending the signal following a direct contact with a base unit, utilizing an indirect wireless contact with a base unit or may utilize a wireless broadcast. The direct contact with a base unit is exampled by having a lead from the base unit which periodically is plugged into the portable monitoring device or having the portable monitoring device periodically placed in physical contact with the base unit wherein matching contacts make contact. The indirect wireless contact with a base unit is exampled by an infrared link as conventionally known for communication between detached electronic equipment, as exampled by such communication between a desktop computer and a laptop computer. The wireless broadcast is exampled by cellular or radio broadcast.

The portable monitoring device may immediately transfer a signal containing data following receipt of the data or immediately following creation of the data. Alternatively, the portable monitoring device may have means to allow for onboard storage of data for batch transfer at a later time. When batch transfer is employed, such transfer may be on a routine schedule via wireless transmission, or may be established on a less rigid schedule over ground based system, as exampled by phone lines.

The means to send a signal may be performed by various types of equipment conventionally known in the art depending upon the type of signal being sent. Many of these methods may be employed with the present invention.

FIG. 1 depicts a transmit antenna 116 contained within portable monitoring device 30. Transmit antenna 116 is capable of broadcasting a signal 117 which is received by receiving tower 36 which, in turn, transfers such signal to central location 32.

FIG. 4 depicts short range transmission antenna 80 contained within portable monitoring device 46. Short range transmission antenna 80 is capable of broadcasting signal 84 which is received by short range reception antenna 76 of secondary transportable device 48. FIG. 4 also depicts long range transmission antenna 72 contained within secondary transportable device 48. Long range transmission antenna 72 is capable of broadcasting a signal 118 which is received by receiving tower 36 which, in turn, transfers such signal to central location 32.

FIG. 6 depicts a short range transmission antenna 80 contained within portable monitoring device 46. Short range transmission antenna 80 is capable of broadcasting a signal 122 which is received by short range reception antenna 96 of stationary device 88. FIG. 6 also depicts phone line 92 of stationary device 88 which is capable of transmitting a signal, not shown, which is received by the central location, not shown in this view.

Temporal Marking Means

In certain situations it is desired to provide for an indication of when certain select references, more fully described below, were generated. This desire is a requirement when the reference is going to be stored for historic reference, also more fully described below. The term temporal, as used herein, carries the common or conventional definition meaning 'of or pertaining to time'. Therefore, the term temporal marking refers to marking, or providing a distinct reference, of when in time an event occurred, within at least a range of time references. It is possible to provide for a temporal marking, or time measurement marking, of each reference utilizing equipment on the portable monitoring device contemporaneously with receipt of the signal(s) upon which the reference is based. Alternatively, it is possible to provide for creation of the temporal marking at the time of receipt at the central location. Generally, it is preferred to have such temporal marking contemporaneously created with each reference. It is possible, and in certain situations preferred, to assign a range to each reference. This method is particularly expedient when performing batch transfers from the portable monitoring device. In certain uses a single time range will have several references associated therewith. The term occurrence reference as used herein refers to the end result data created indicative, within at least a range, of when an event occurred.

Figure 7:
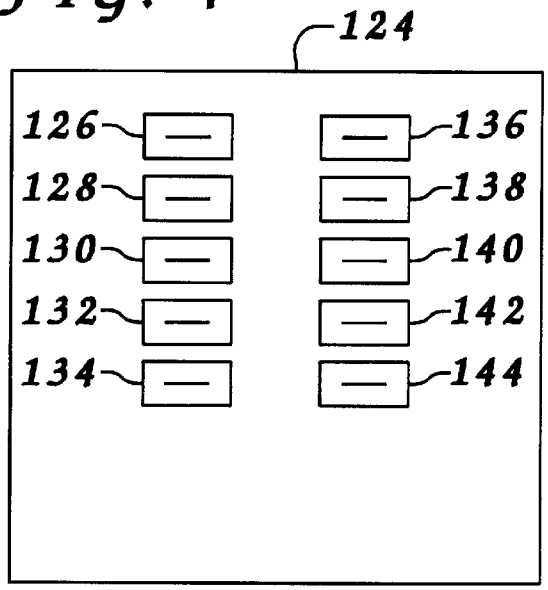
FIG. 7 is a plan view of a block with various bodily signal references and associated occurrence references therein.

FIG. 7 depicts, within a block 124, a series of five bodily signal references 126, 128, 130, 132 and 134, more fully disclosed elsewhere herein, each having an associated occurrence reference 136, 138, 140, 142 and 144 respectively. Each bodily signal reference 126, 128, 130, 132 and 134 would have a data string containing information about a respective bodily function, associated therewith. Each associated occurrence reference 136, 138, 140, 142 and 144 would have a set of identifying information which are, or may be converted to, date and time references. In this example each adjacent sequential associated occurrence reference 136, 138, 140, 142 and 144 are a uniform measurement of time apart. Alternatively, each string of bodily function references may have a beginning occurrence reference and an ending occurrence reference. From these occurrence references and the number of uniformly spaced bodily function references it is possible to determine a occurrence reference for each respective bodily function reference.

Figure 5:
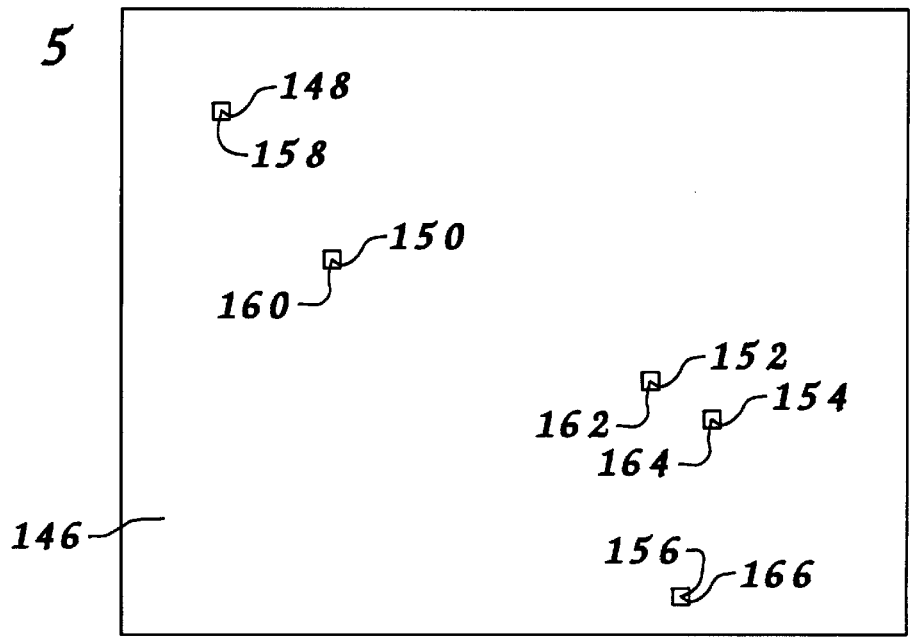
FIG. 5 is a plan view of a block with various position references and associated occurrence references distributed therein.

FIG. 5 depicts, within a block 146, a series of five position references 148, 150, 152, 154 and 156 each having an associated occurrence reference 158, 160, 162, 164 and 166 respectively. Each position reference 148, 150, 152, 154 and 156 would have a set of coordinates, or other acceptable identifying reference, associated therewith. Each associated occurrence reference 158, 160, 162, 164 and 166 would have a set of identifying information which are, or may be converted to, date and time references. In this example each adjacent sequential associated occurrence reference 158, 160, 162, 164 and 166 are a uniform measurement of time apart.

Reference Storage Means

It is often a requirement that bodily signal references be stored along with associated occurrence references indicative of what time span the respective references were associated with in a bodily signal database. It is often a requirement that position references be stored along with associated occurrence references indicative of what time span the respective references were associated with in a locational tracking database. This provides for historic use of the data stored for various useful purposes. These references may be stored in separate databases or they may be stored in a common database, if both types of references are being created within the deployed system.

Numerous methods are known in the art for electronic storage of data which permit subsequent retrieval based upon select models. Many of these methods may be employed with the present invention. It being understood that such storage of bodily signal references, position references and associated occurrence references are not required for all embodiments of the invention.

When required, each reference will be stored along with the associated occurrence reference. As mentioned, it is possible to assign a single range to a series of associated occurrence references. Alternatively, it is possible to provide for storage of select references taken from the totality of references available. One example uses a computer program which examines the series of references and identifies sequential strings of references within the series which do not vary beyond a predetermined tolerance range from all other references within the string. The computer program would then purge from the system all data between the first reference and the last reference within the string. This is particularly expedient where the monitored person is stationary for a long period of time, as example by sleeping for a number of hours in a generally stationary location.

FIG. 3 depicts a computer 168 having a storage device 170. Computer 168 is linked via coupling 52 to receiving tower 36 which receives a signal 172 which contains data transmitted by a transmit antenna 174 of a portable monitoring device 176. The information contained in signal 172, following any conversion, if required, is stored within storage device 170 as a database 178. Database 178 may contain a sequence of data references 180. Data references 180 may be either position references and/or bodily signal references. Database 178 may also contain a sequence of associated occurrence references 182 containing information about the time, or period of time, associated with each respective data reference 180.

Monitoring Means

A monitoring of a person under the present invention may include a determination of measurements of select bodily functions of the person. Examples of such bodily functions include blood pressure, (systolic and diastolic), heart beat rate, respiration rate, bodily temperature, blood oxygen level and blood alcohol level, amongst others. Devices are conventionally known in the art which may measure such functions in a non invasive manner (without requiring mechanical penetration of the body of the monitored person). These devices are exampled by passive contact of a portion of the device with the skin of the person or by manipulation of a portion of the device by the person, as exampled by a tubular member into which the person breathes. When passive contact is utilized the contact may be with a sensor positioned on the portable monitoring device or may be with a patch attached to the skin of the monitored person. Such patches are known in the art capable of monitoring bodily functions or which measure for the presence of select drugs in the system of the monitored person. When bodily functions are being monitored, it is possible to provide for an elimination of the normal strong desire that the portable monitoring device comprise tamper detection means. Many different medical test equipment exists in the art to perform various test to determine a respective specific status of a patient. Numerous of these medical test equipment may be utilized within a system under the present invention. These include select members of those medical test equipment which rely upon manipulation of a composition (such as a chemical or a drug) during the test process.

Measurements of bodily functions of a person may be evaluated to determine what type of activity the person is likely to be engaged in, or recently engaged in, at the time the measurements were taken. Most persons are unable to consciously regulate such bodily functions to a sufficient extent to allow for the measurements to indicate a general type of activity radically different from the actual general type of activity being performed.

While it is preferred to utilize sensors which may make their readings based on no more than passive contact with the monitored person, it is possible to provide for implantation of a sensor under the skin of the monitored person. Such an implanted sensor would transfer, preferably by wireless transfer, a signal to a receiving unit in possession of the monitored person and preferably contained within a portable monitoring device attached to the monitored person.

Figure 8A:
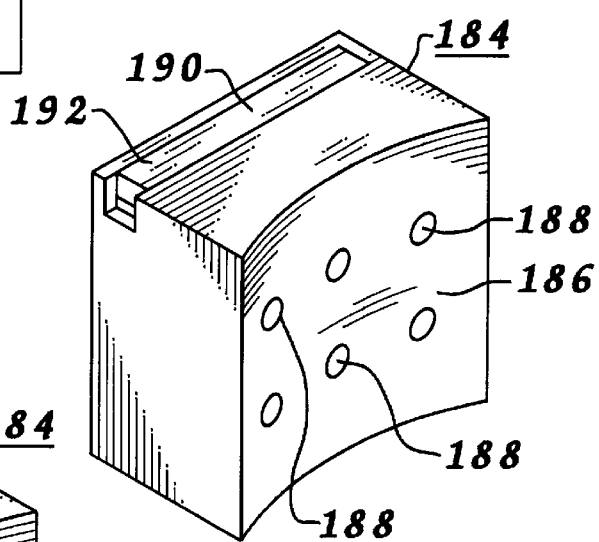
FIG. 8a and FIG. 8b are perspective views of a portion of an embodiment of a portable monitoring device in alternative operational positions.
Figure 8B:
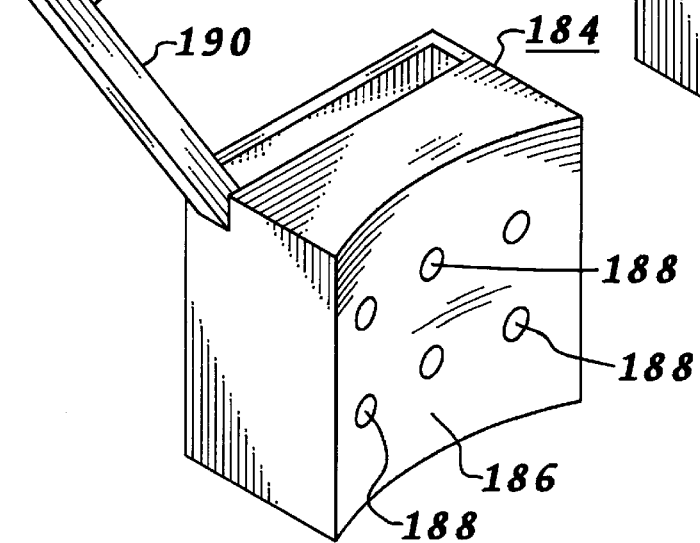

FIG. 8a and FIG. 8b depict a portable monitoring device 184 having a skin contact surface 186 which would be held in contact with the skin of the monitored person, not shown, during deployment. This deployment may be on any portion of the body of the monitored person required to provide for adequate testing of the bodily function(s) being monitored. Skin contact surface 186 has a series of contacts 188 which, when held in contact with human skin, may provide input to provide for a measurement of various body functions of the person. These contacts 188 may read, and/or produce various signals including electrical impulses and/or pressure changes and/or light reflective properties. This provides for other connected equipment within portable monitoring device 184 to make determinations, based on input from contacts 188, of select bodily functions including blood pressure, heart beat rate, respiration rate, bodily temperature and blood oxygen level. A breath tube 190 is depicted in a stored position 192, see FIG. 8*a,* and in a deployed position 194, see FIG. 8*b*. Breath tube 190 may be deployed when required and the monitored person may be required to blow therein to allow for measurement of blood alcohol level.

Bodily Signal Reference Creation Means

It is conventionally known in the art to convert measurements of each applicable bodily function to a data reference. These data references, or bodily signals, generally match conventional measurement methods or at least allow ready conversion to conventional measurement methods. One example of such a conventional measurement method is conversion of the respective bodily function cycle to a number of repetitions in a defined period of time such as one (1) minute. Other examples include measurement of a pressure or a lower and upper pressure range. Any conventional method may be utilized to reduce the measurement taken to a data reference.

Figure 9A:
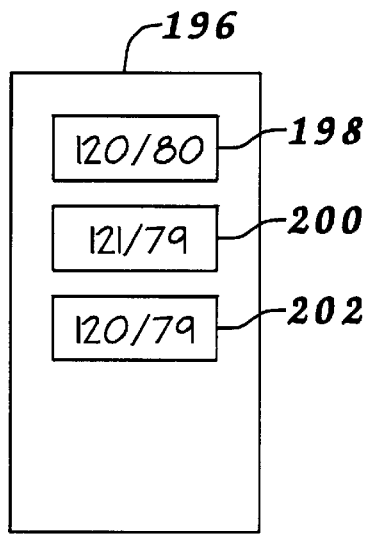
FIG. 9a through FIG. 9f are plan views of various data blocks.

FIG. 9*a* depicts a data block 196 comprised of a series of three (3) bodily signal references 198, 200 and 202 containing data indicative of blood pressure readings for a monitored person, not shown.

Figure 9B:
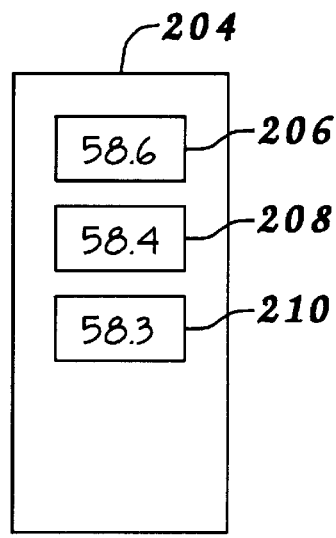

FIG. 9*b* depicts a data block 204 comprised of a series of three (3) bodily signal references 206, 208 and 210 containing data indicative of heart beat rate readings for a monitored person, not shown.

Figure 9C:
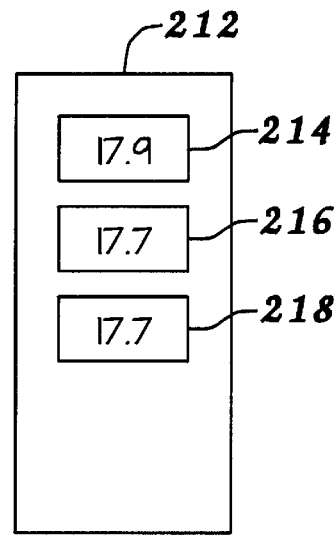

FIG. 9*c* depicts a data block 212 comprised of a series of three (3) bodily signal references 214, 216 and 218 containing data indicative of respiration rate readings for a monitored person, not shown.

Figure 9D:
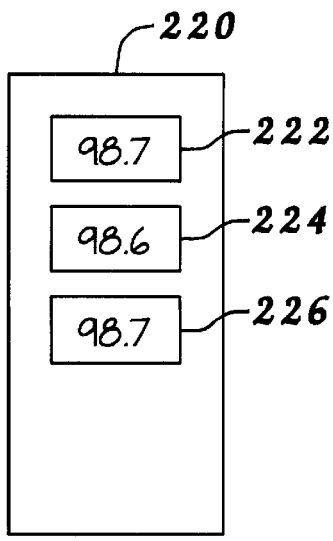

FIG. 9*d* depicts a data block 220 comprised of a series of three (3) bodily signal references 222, 224 and 226 containing data indicative of bodily temperature readings for a monitored person, not shown.

Figure 9E:
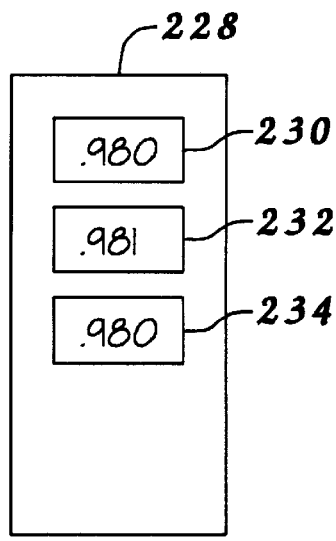

FIG. 9*e* depicts a data block 228 comprised of a series of three (3) bodily signal references 230, 232 and 234 containing data indicative of blood oxygen readings for a monitored person, not shown.

Figure 9F:
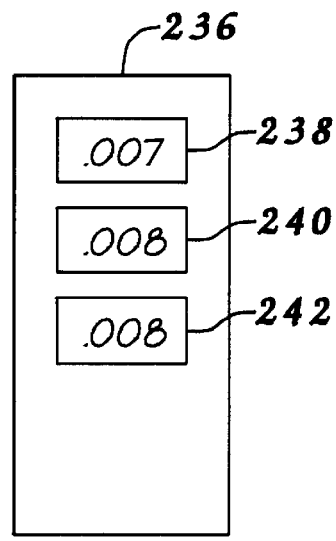

FIG. 9*f* depicts a data block 236 comprised of a series of three (3) bodily signal references 238, 240 and 242 containing data indicative of blood alcohol readings for a monitored person, not shown.

Any of the conversion methods conventionally known in the art may be utilized to convert applicable sensor data into respective data block 196, 204, 212, 220, 228 or 236.

Positional Determining Means

Various systems, and devices based upon those systems, exist to provide for a determination of a positional location. Several of these system are capable of making such a determination within a fairly narrow range of measurement. One group of such systems rely upon transmissions from satellites in orbit around our planet. Another group relies upon transmissions from ground based transmitters. Another group relies upon transmissions from a combination of satellites and ground based transmitters. Several of these systems, as exampled by differential global positioning systems, include the ability to identify an elevational height, or altitude, as well as a locational position. Such determination may be extremely desirable where the positional location is within a building having multiple floors such as skyscrapers.

Without regard for the transmission system employed to generate a signal, or signals, each portable monitoring device may routinely receive at least one signal. This signal, or signals, is then capable of, through a mathematical computation, being reduced to a position reference indicative of a specific location, within a predetermined range of measurement. It is possible that the mathematical computation will be performed by a device located within the portable monitoring device with the actual position reference being sent within the signal of the transmitting means of the portable monitoring device. Alternatively, raw data may be sent within the signal of the transmitting means of the portable monitoring device with the mathematical computation occurring subsequent to receipt of the signal by the transmission acquisition means, as exampled by at the central location.

It is possible, and preferred in certain deployments, to have a reliance upon a primary transmission system and at least one backup transmission system. The signal(s) from the primary transmission system may be indefinite or totally absent, in which case the mathematical computation based on the signal(s) received by the portable monitoring device from the primary transmission system would be incapable of determining a position reference. In that case the portable monitoring device would switch through any backup transmission systems until the received signal(s) was present and of a quality from which a position reference might be computated.

The example which follows makes use of Global Positioning Satellites (G.P.S.), as conventionally known in the art, for determining a locational position of the respective portable monitoring device. Selection of this method of determining locational position is due to the wide coverage area and the accuracy afford by such usage. Numerous other methods, all conventionally known in the art, are adaptable for usage with the present invention.

FIG. 3 depicts satellite 106, satellite 108 and satellite 110 which each routinely generate signals 100, 102 and 104 respectively. Reception antenna 98 of portable monitoring device 176 receives such signals 100, 102 and 104. Portable monitoring device 176 may then transfer such signals, using transmit antenna 174, within signal 172, along with any distinct signal(s) created within portable monitoring device 176 which may be required to computate a position reference 244, to receiving tower 36. Alternatively, portable monitoring device 176 may perform the required mathematical computations and transfer signal 172 containing position reference 244.

FIG. 4 depicts secondary transportable device 48 and portable monitoring device 46. Secondary transportable device 48 contains structures, as disclosed above, which enable a determination of a position reference 246 indicative of its positional location. Secondary transportable device 48 further contains a first locational device 248 while portable monitoring device 46 contains a second locational device 250. First locational device 248 and second locational device 250 provide for a determination of a general directional indication and a general spacing indication wherein a positional location 252 of portable monitoring device 46 may be made relative to position reference 246 of secondary transportable device 48. In such a manner it is possible to make a determination, utilizing methods conventionally known in the art, of a position reference 254 (within a reasonable variation) of portable monitoring device 46 without requiring more complicated equipment located on portable monitoring device 46.

Position Reference Creation Means

Numerous reference methods, as conventionally known in the art, may be employed to define each position reference, as exampled by a set of coordinates. One example of these coordinate references is those based upon a set of latitude, in degrees to a desired degree of precision, and longitude, in degrees to a desired degree of precision, references. Another example of these coordinate references include those based upon a set of distance, in any conventional measurement distance, and angular orientation, as exampled by degrees, references from a fixed position reference.

Figure 10:
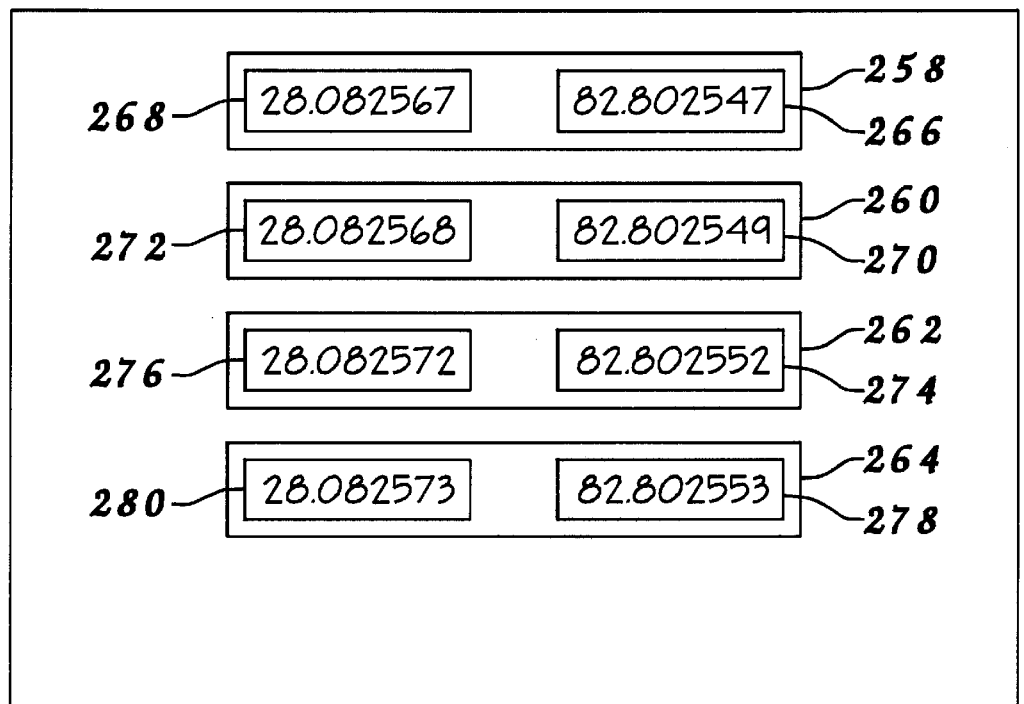
FIG. 10 is a plan view of a database.

FIG. 10 depicts a database 256 having a series of coordinates 258, 260, 262 and 264. Coordinate 258 comprises a longitudinal reference 266 and a latitude reference 268 which identifies a unique locational position. Coordinate 260 comprises a longitudinal reference 270 and a latitude reference 272 which identifies a unique locational position. Coordinate 262 comprises a longitudinal reference 274 and a latitude reference 276 which identifies a unique locational position. Coordinate 264 comprises a longitudinal reference 278 and a latitude reference 280 which identifies a unique locational position. Various methods may be utilized to create the various coordinates 258, 260, 262 and 264.

Intervention Means

It is possible to provide for a mechanical intervention to dissuade a monitored person from a definable course of action. Many such mechanical interventions are conventionally known in the art and many of these may be adapted for use within the present invention. Such applicable mechanical interventions may involve administration of a medicine or introduction of a physical action which act as a deterrent to discourage continuation of the definable course of action. Examples of such medications include those which act to partially sedate or to completely incapacitate the monitored person. One example of such physical action involves introduction of an electrical shock to the monitored person.

When intervention means are provided it is a requirement that structures be positioned upon the monitored person. This will involve placement upon the portable monitoring device or upon a secondary device similarly attached to the monitored person. Typically this will require surrounding engagement of the monitored person. This may involve placement at a wrist, arm, leg, ankle, neck, chest, waist or other suitable portion of the body. Alternatively, implantation may be employed for at least a portion of the device under the skin of the person. When intervention means are included it is a requirement that structures be present to provide for activation of the intervention means. This activation may be provided without additional communication beyond that within the device attached to the monitored person. Alternatively, this activation may be provided based upon reception of a signal by the device attached to the monitored person from an outside location such as from the central location.

Figures 11, 12:
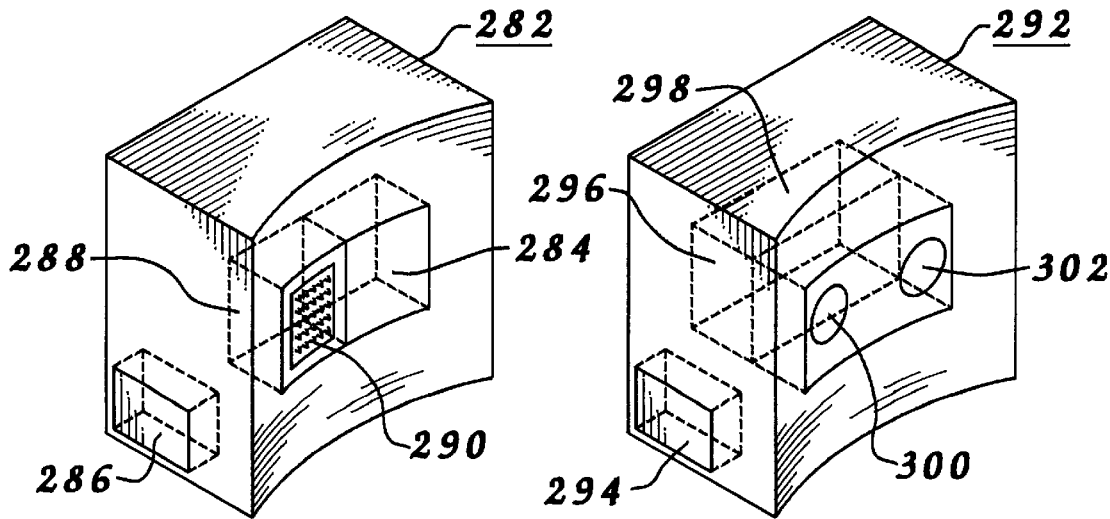
FIG. 11 is a perspective view of an embodiment of a portable monitoring device.
FIG. 12 is a perspective view of an embodiment of a portable monitoring device.

FIG. 11 depicts a portable monitoring device 282 having a medication container 284 having a medication, not shown, contained therein. The medication may have a composition which provides for entry into the monitored person by absorption through the skin or which requires injection through the skin. A control device 286 provides for activation of a delivery system 288 when it is required that the medication be introduced into the monitored person. Delivery system 288 provides for micro needles 290, as conventionally known in the art, to be deployed for injection of the medication into the monitored person. Alternatively, a conventional injection needle may be so deployed to provide for entry of the medication. Alternatively, delivery system 288 may release, as exampled by spraying, the medication of a absorbent type onto the skin of the monitored person where the medication may be absorbed for entry into the monitored person.

FIG. 12 depicts a portable monitoring device 292 having a control device 294 and a delivery system 296. Control device 294 may cause activation of delivery system 296 wherein a high voltage electrical shock, as conventionally known in the art, from a power supply 298 may be delivered to the monitored person via a first electrode 300 and a second electrode 302.

Various specific tamper detection methods may be employed to prevent tampering with applicable portable monitoring devices where such tampering is intended to prevent introduction of the medication or the electrical shock to the monitored person.

While applicable to several embodiments of the present invention, an active intervention by a device located on the restrictee portable monitoring device is particularly applicable to the dual tracking system. One example involves when the restrictee person enters a predefined perimeter around the restrictor person, and when there is a prior conclusion reached by proper authorities that the restrictee person poses a physical threat to the restrictor person, the portable monitoring device may be activated to disable the restrictee person using any of the method conventionally known in the art. One example of a method of disabling the restrictee person would be through injection of a tranquilizer. Another example would be to stun the restrictee person with a high voltage charge.

Figure 13A:
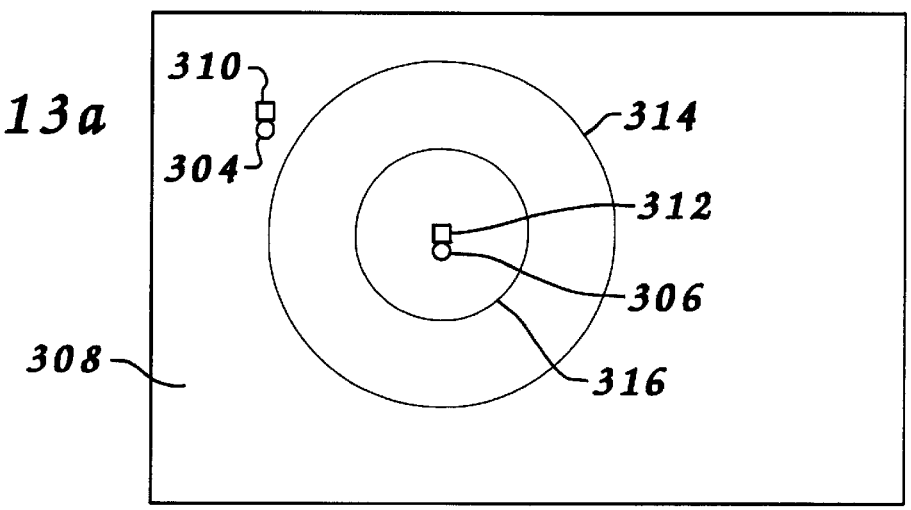
FIG. 13a through FIG. 13c are plan views of a block in various alternative orientations.
Figure 13B:
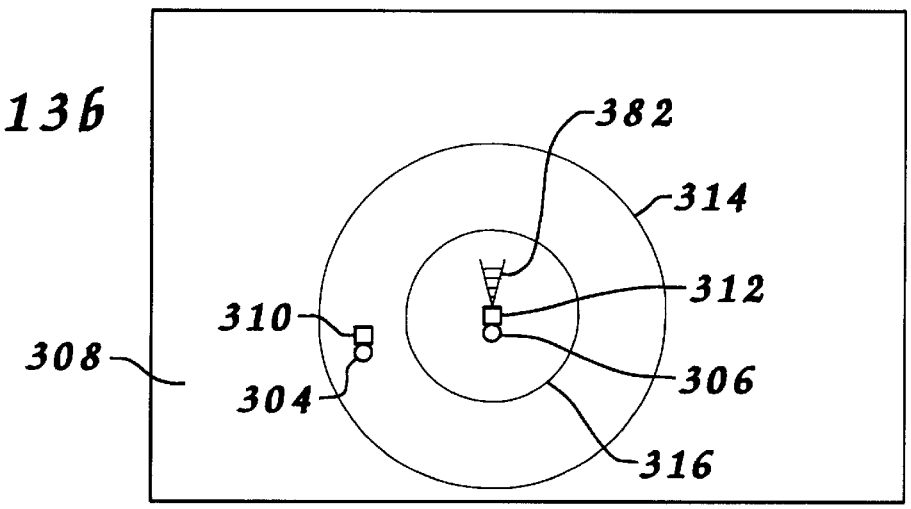
Figure 13C:
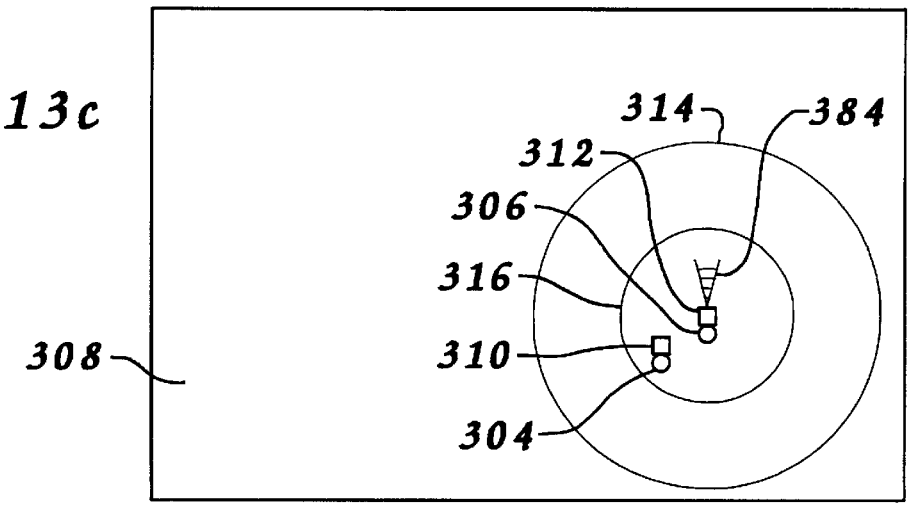

FIG. 13a through FIG. 13c depict a restrictee person 304 and a restrictor person 306 within a block 308. Restrictee person 304 has attached thereon a restrictee portable monitoring device 310. Restrictor person 306 carries with them a restrictor portable monitoring device 312. A first perimeter 314 radially surrounds restrictor portable monitoring device 312. A second perimeter 316, being smaller than first perimeter 314, radially surrounds restrictor portable monitoring device 312. Perimeters 314 and 316 are variable and move with restrictor portable monitoring device 312 as restrictor person 306 carries it about block 308.

In FIG. 13a restrictee person 304 and restrictee portable monitoring device 310 are outside of both first perimeter 314 and second perimeter 316. In this instance no activation of the intervention means is performed. In FIG. 13b restrictee person 304 and restrictee portable monitoring device 310 are inside of the first perimeter 314 while outside of second perimeter 316. In FIG. 13c restrictee person 304 and restrictee portable monitoring device 310 are inside of both first perimeter 314 and second perimeter 316 and an intervention is activated to disable restrictee person 304.

Bodily Signal Conditional Database

It is a desire to store various bodily signal conditional references created for each applicable respective monitored person being monitored. These conditional references would include a set of references, either inclusive or exclusive, which would provide for a comparison to determine if the respective monitored person was outside of an acceptable range for the particular bodily signal, or signals, being monitored. Such a database could be used to identify unacceptable conduct or to identify potentially dangerous medical conditions.

Figure 14:
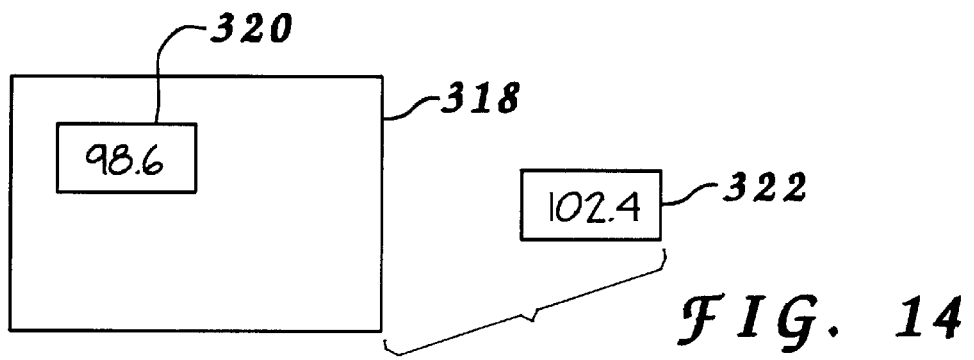
FIG. 14 is a plan view of a bodily signal conditional database and a comparative bodily signal reference.

FIG. 14 depicts a bodily signal conditional database 318 having a baseline measurement 320 for a specific bodily function. A comparative bodily signal reference 322, disclosed elsewhere herein, may be compared to baseline measurement 320 utilizing a mathematical computation which would establish an acceptable range to determine if the comparative bodily signal reference 322s within the range, or acceptable, or outside of the range, or unacceptable.

Figure 15:
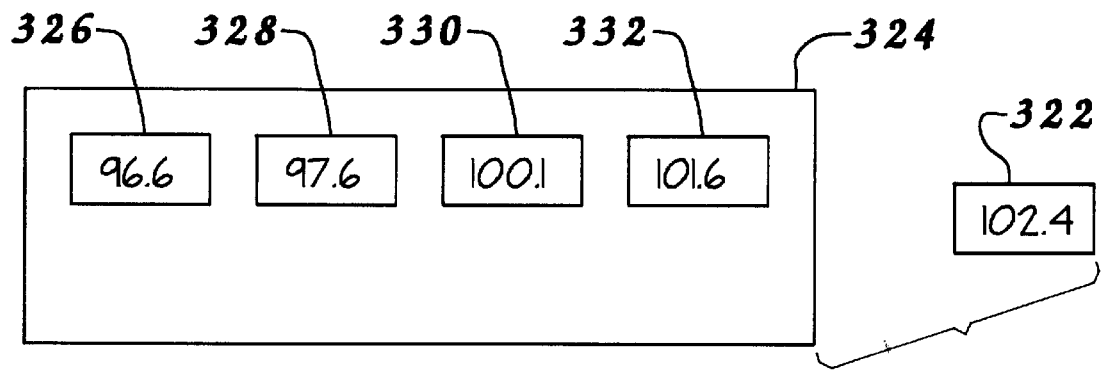
FIG. 15 is a plan view of a bodily signal conditional database and a comparative bodily signal reference.

Alternatively, as exampled by a bodily signal conditional database 324 as depicted in FIG. 15 may have multiple comparative references specific to the bodily function being monitored. In this example, a dangerous lower range 326, a warning lower range 328, a warning upper range 330 and a dangerous upper range 332 may be defined within bodily signal conditional database 324. If comparative bodily signal reference 322 reaches, or passes, either warning lower range 328 or warning upper range 330 a first signal would be produced for subsequent action by the overall system. If comparative bodily signal reference 322 subsequently reaches, or passes, either dangerous lower range 326 or dangerous upper range 332 a second signal would be produced for subsequent action by the overall system.

The bodily signal conditional database could be identical for all monitored persons, could be specific to the monitored person or could be based on specific characteristics of the monitored person as exampled by age, weight, sex, other factors or any desired combination thereof.

Positional Conditional Database

It is a desire to store various positional conditional references created for each applicable respective monitored person being monitored. These conditional references would include a set of references, either inclusive or exclusive, which would provide for a comparison to determine if the respective monitored person was either inside of an allowable roaming area or outside of an excluded roaming area, or areas, for the respective monitored person.

Figure 17:
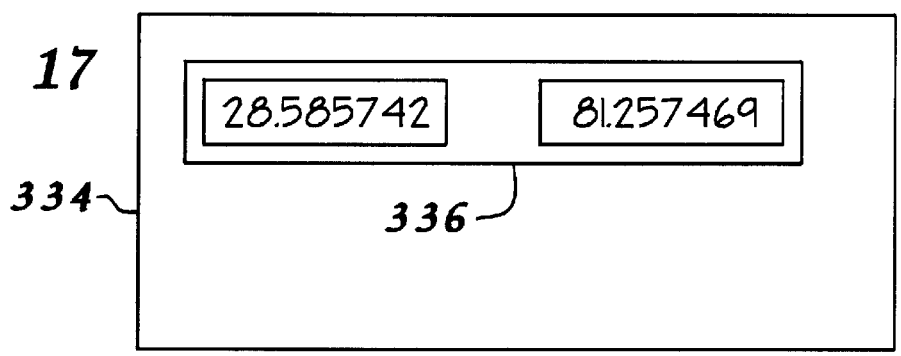
FIG. 17 is a plan view of a positional conditional database.

FIG. 17 depicts a positional conditional database 334 having a reference 336. A specific position reference, disclosed elsewhere herein, may be compared to reference 336 utilizing a mathematical computation which would establish if the comparative position reference was acceptable or unacceptable in comparison to reference 336. The mathematical computation may define complex perimeters relative to reference 336 or may define a radial perimeter thereabout.

Figure 18:
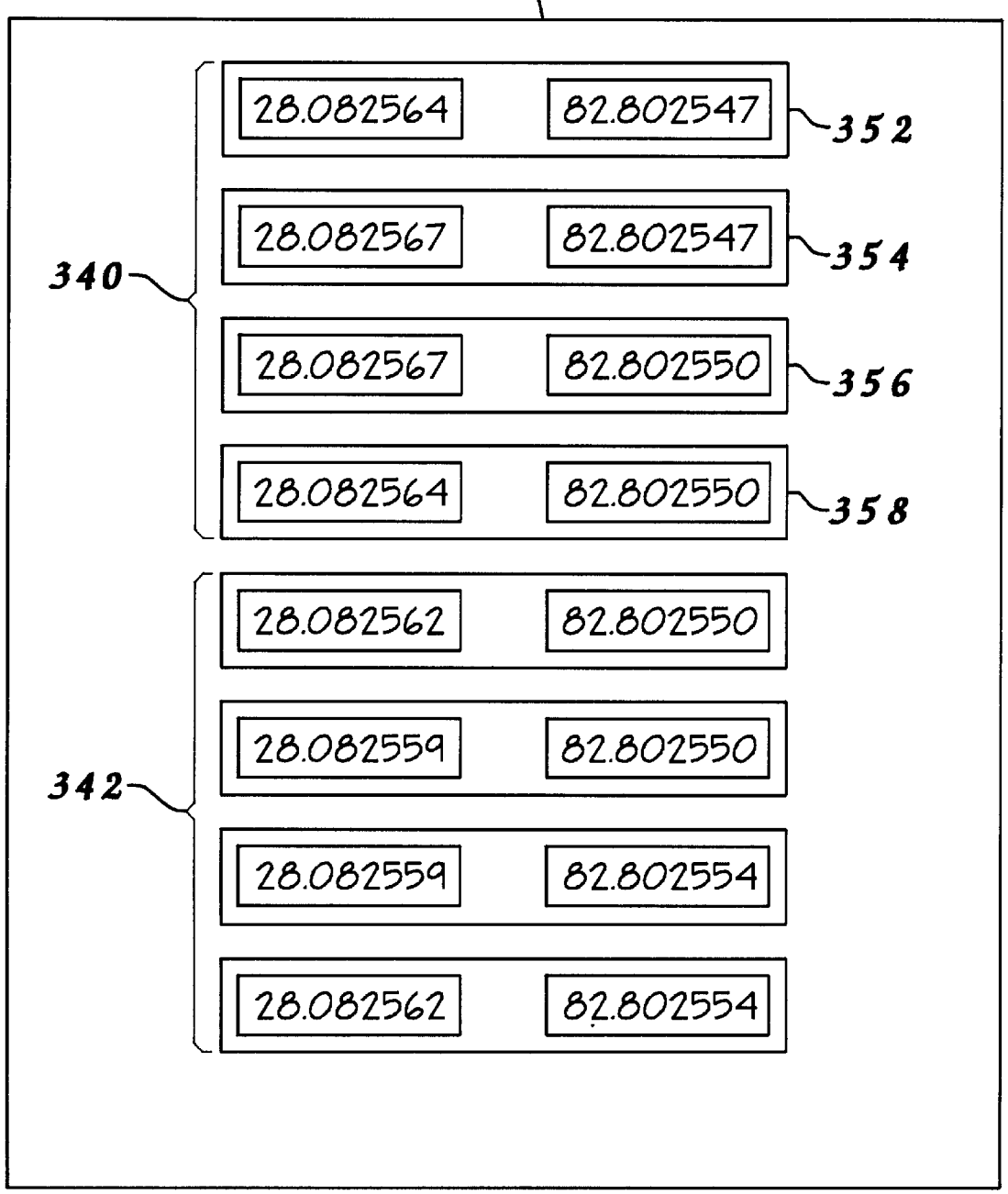
FIG. 18 is a plan view of a positional conditional database.

FIG. 18 depicts a positional conditional database 338 having a first series of references 340 and a second series of references 342. Each series of references 340 or 342 define included locations where presence is allowed, excluded locations where presence is not allowed or a combination thereof. Positional conditional database 338 may have any desired number of such series as required to adequately define included locations, excluded locations or a combination thereof. A specific position reference, disclosed elsewhere herein, may be compared to series of references 340 or 342 utilizing a mathematical computation which would establish if the comparative position reference was acceptable or unacceptable in comparison to the series of references.

Figure 19A:
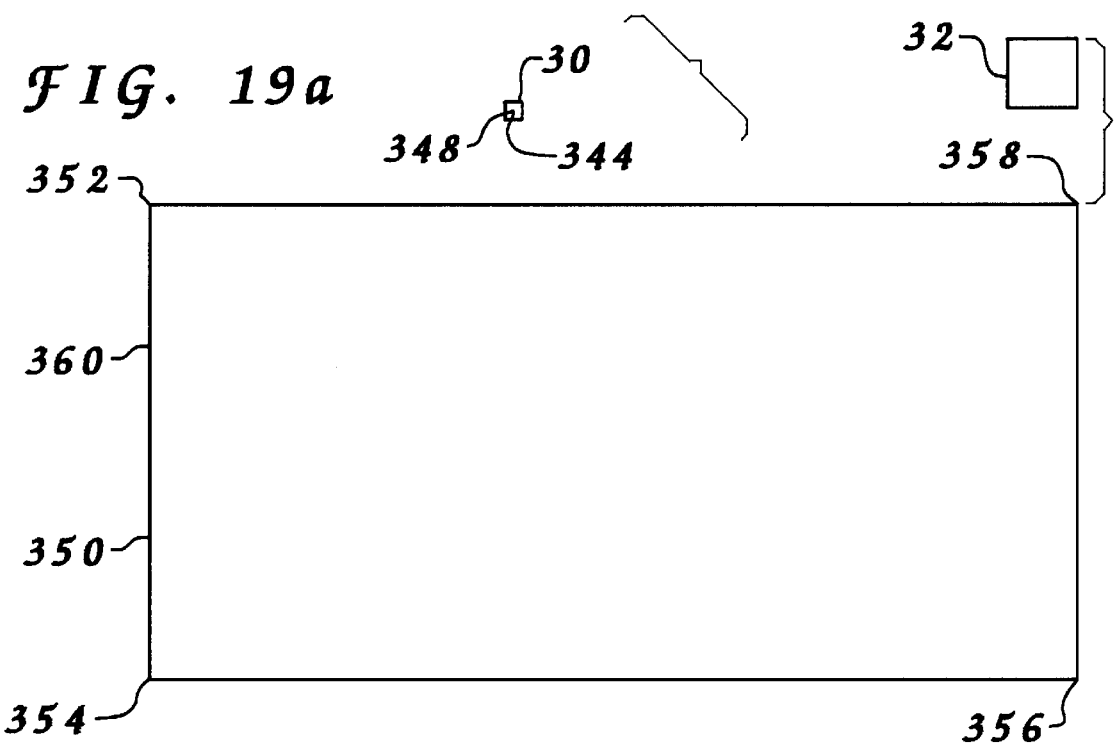
FIG. 19a and FIG. 19b are plan views of a block in various alternative orientations.
Figure 19B:
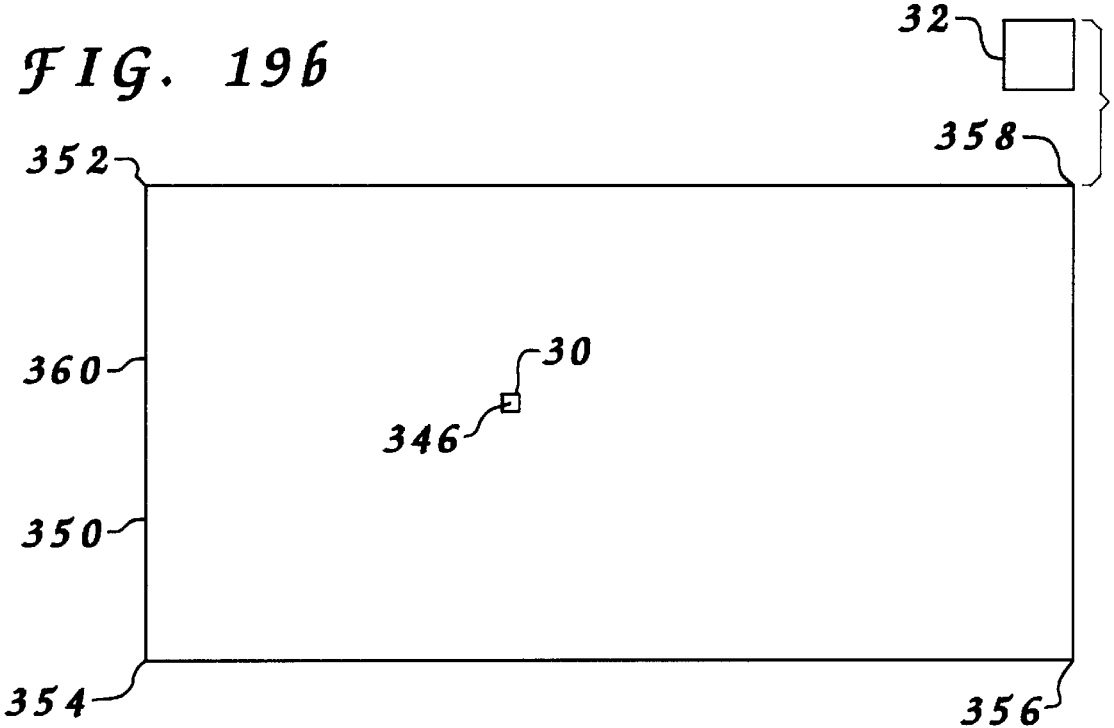

FIG. 19a and FIG. 19b depict a position reference 344 and a position reference 346 respectively. Position reference 344 is received by central location 32 subsequent to transmission by portable monitoring device 30, more fully described elsewhere herein. (Position reference 344, a numeric value defines a location reference 348 is substantially identical to placement of portable monitoring device 30.) An excluded site 350 is defined by four (4) references 352, 354, 356 and 358 of first series of references 340, see FIG. 18, which are positioned at each corner thereof. It being understood that a computer program, as programable using methods conventionally known in the art, may be created which is capable of defining a boundary 360 based on references 352, 354, 356 and 358. Similarly, such a program could define any conceivable outline of a specific boundary. Boundary 360 extends around excluded site 350. The program could also be programed to determine if any specific position reference is inside of boundary 360. FIG. 19a depicts position reference 344 outside of excluded site 350. In this instance the program would not indicate, or otherwise report, a violation of excluded site 350. FIG. 19b depicts position reference 346 positioned within excluded site 350. In this instance the program would indicate, and report, a violation of excluded site 350 by portable monitoring device 30.

Comparison Means

There exist two modes of operation for comparison of references, either bodily signal and positional, of each monitored person. The first mode is real time comparison and the second is historic comparison. The real time comparison involves comparison of the reference to the applicable bodily signal conditional database or positional conditional database or, in the case of positional determination, proximity to other variable position references. (The term real time comparison is not meant to convey simultaneous comparison, but rather may have the actual comparison occurring at a slightly later time.) The historic comparison involves comparison of the applicable reference, either bodily function or positional, to a later defined set of comparative data. It is possible to provide for such comparison of data to the respective references to be employed as evidence during a legal proceeding, either a criminal proceeding or a civil proceeding. The comparison may be made directly within the portable monitoring device by having the respective conditional database contained therein. Alternatively, the comparison may be made at the central location by having the respective conditional database stored thereat.

a. Immediate Comparison

Comparison of the bodily signal references against the bodily signal conditional database for a respective portable monitoring device may occur immediately subsequent to creation thereof, either within the portable monitoring device or when received by the central location. Comparison of the position references against the positional conditional database for a respective portable monitoring device may occur immediately subsequent to creation thereof, either within the portable monitoring device or when received by the central location. (In certain situations it is not a requirement that all deployed portable monitoring device have securing means or tamper detection means, as more fully described herein.)

FIG. 19a and FIG. 19b depict position reference 344 and position reference 346 respectively. Position reference 344 is received by central location 32 subsequent to transmission by portable monitoring device 30, more fully described elsewhere herein. (Position reference 344 a numeric value defines location reference 348 is substantially identical to placement of portable monitoring device 30.) Excluded site 350 is defined by four (4) references 352, 354, 356 and 358 which are positioned at each corner thereof. It being understood that a computer program, as programable using methods conventionally known in the art, may be created which is capable of defining boundary 360 based on references 352, 354, 356 and 358. Similarly, such a program could define any conceivable outline of a specific boundary. Boundary 360 extends around excluded site 350. The program could also be programed to determine if any specific position reference is inside of boundary 360. FIG. 19a depicts position reference 344 outside of excluded site 350. In this instance the program would not indicate, or otherwise report, a violation of excluded site 350. FIG. 19b depicts position reference 346 positioned within excluded site 350. In this instance the program would indicate, and report, a violation of excluded site 350 by portable monitoring device 30.

FIG. 14 depicts comparative bodily signal reference 322 which is compared to baseline measurement 320 of bodily signal conditional database 318 in real time. Variation of comparative bodily signal reference 322 beyond a predetermined range from baseline measurement 320 results in a predetermined activation of a response by the system.

b. Historic Comparison

It is possible to historically utilize recorded bodily signal references to determine what type of activity a specific monitored person was engaging in at a specific time. This type of comparison may be used for several reasons, including as a tool for law enforcement agencies.

When position references are stored they may be utilized to determine if any of the monitored persons were within a defined area, as exampled by within the boundaries of a crime scene, during a defined period of time, as example by a window of opportunity in which time span the crime could have been committed. Such comparison may be useful to eliminate a suspect for a given crime.

Figure 20:
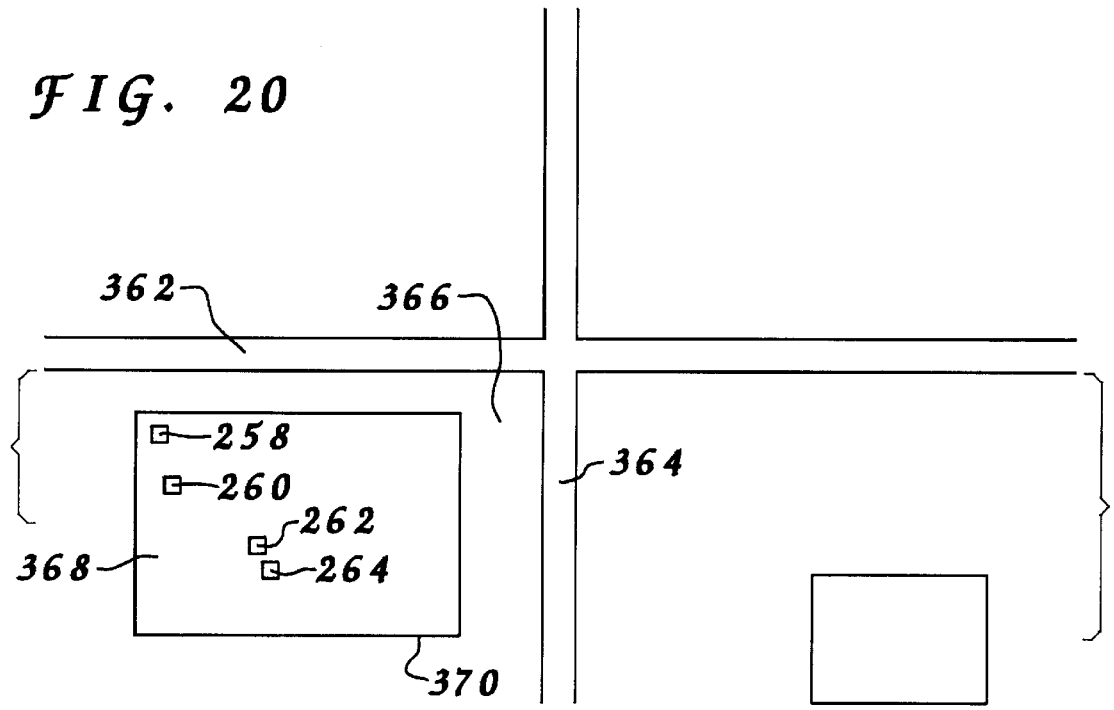
FIG. 20 is a plan view of an intersection of two streets and a comparative location reference.

FIG. 20 depicts a street 362 and a street 364 intersecting one another. A vacant lot 366 is situated on one corner of street 362 and street 364. A comparative location reference 368 has been identified and is surrounded by a boundary 370. A comparative temporal reference, not shown, which has a range of temporal references, has been entered. In this example boundary 370 falls completely within vacant lot 366.

A computer program, not shown, has examined all records within database 256, see FIG. 10, and has identified coordinate 258, coordinate 260, coordinate 262 and coordinate 264 which have associated occurrence references, not shown, which fall within the comparative temporal reference. Each coordinate 258, 260, 262 and 264 were created as a result of a single portable monitoring device, not shown. Therefore, it is possible to determine which monitored person, if any, were within the later created comparative location reference 368 during a period of time represented by the comparative temporal reference.

Figure 16:
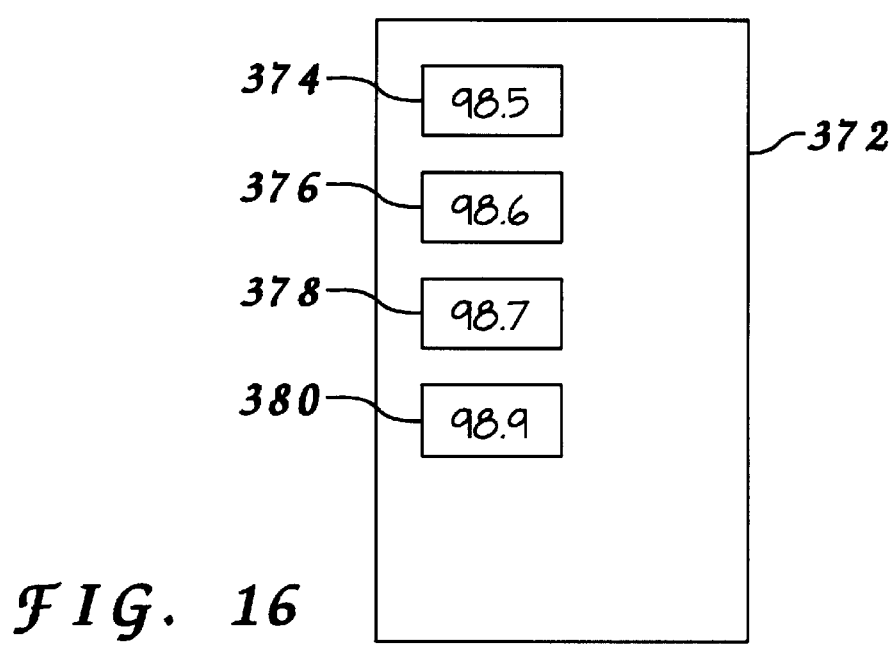
FIG. 16 is a plan view of a bodily signal conditional database.

FIG. 16 depicts a bodily signal reference database 372 having stored therein a series of bodily signal references 374, 376, 378 and 380. These references may be historically examined to determine the status of the monitored person.

Dual Tracking System

It is possible to provide for monitoring of a pair of persons to monitor the behavior of a first person, a restrictee person, relative to a second person, a restrictor person. There exist several possible combinations within the general concept of dual tracking. It is possible to have a clear pairing where there exists one restrictee person and one restrictor person.

It is possible to have a single restrictee person monitored relative to a plurality of restrictor persons. It is possible to have multiple restrictee persons monitored relative to a single restrictor person.

The dual tracking system is applicable to several situations, but is particularly expedient in the enforcement of court issued restraining orders. The immediate comparison, the historic comparison or a combination of both types of comparison may be used. The historic comparison may be useful as evidence during a subsequent legal proceeding, as example as proof of violation of the court issued restraining order.

A computer program may be designed which defines a perimeter around the restrictor person of the pair of monitored persons which is updated depending upon the movement of the restrictor person. When the restrictee person enters within the perimeter a notification is given of such violation. This notification can be to an oversight authority, to the applicable restrictor person, or to both. When notification is given to the restrictor person communication therewith may be by any of the methods conventionally known in the art. Preferably, such notification would be received by the restrictor portable monitoring device which would then inform the restrictor person. It is also possible that human personnel at the central location would establish cellular communication with the restrictor person and advise the restrictor person of the position of the restrictee person relative to the restrictor person.

It is possible to provide for several unique perimeters around the restrictor person. Each unique perimeter would have a predefined distance measurement from the restrictor person. It is also possible to define various distinct notifications of violation of the different unique perimeters.

The computer program could be designed such that the position references of the restrictor person are not stored. This protects the privacy of the restrictor person which has not surrendered any of their rights. Alternatively, it is possible to store the applicable position references of the restrictor person only when the restrictee person is with a predetermined distance measurement of the restrictee person, as exampled by the perimeter previously described. This allows for the retention of such records for use during a subsequent legal proceeding. Such a program could be designed which retains the position references for a specific period of time, adding new position references and purging the oldest position references. Then, when a violation occurs all existing location references within the system could be stored. Storage would continue until a predetermined time following cessation of the violation. This arrangement allows for the preservation of the restrictor person's position references for a predetermined period of time prior to the violation, the entire period of time during the violation and for a predetermined period of time following the violation. The restrictee person's position references can similarly be stored, or all such data may be stored within the locational tracking database.

FIG. 13a through FIG. 13c depict restrictee person 304 and restrictor person 306 within block 308. Restrictee person 304 has attached thereon restrictee portable monitoring device 310. Restrictor person 306 carries with them restrictor portable monitoring device 312. First perimeter 314 radially surrounds restrictor portable monitoring device 312. Second perimeter 316, being smaller than first perimeter 314, radially surrounds restrictor portable monitoring device 312. Perimeters 314 and 316 are variable and move with restrictor portable monitoring device 312 as restrictor person 306 carries it about block 308. In FIG. 13a restrictee person 304 and restrictee portable monitoring device 310 are outside of both first perimeter 314 and second perimeter 316. In this instance no notification is given. In FIG. 13b restrictee person 304 and restrictee portable monitoring device 310 are inside of first perimeter 314, yet outside of second perimeter 316, and a first notification 382 is given. First notification 382 is exampled by a first beeping sound coming from restrictor portable monitoring device 312. In FIG. 13c restrictee person 304 and restrictee portable monitoring device 310 are inside of both first perimeter 314 and second perimeter 316 and a second notification 384 is given. Second notification 384 is exampled by a second beeping sound coming from restrictor portable monitoring device 312. The second beeping sound would be distinct from the first beeping sound.

With respect to the above description then, it is to be realized that the optimum dimensional relationships for the parts of the invention, to include variations in size, material, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A monitoring system to provide for monitoring a plurality of monitored persons, the monitoring system comprising:
   a) a portable monitoring device for each of the monitored persons, each portable monitoring device comprising:
      1) securing means to provide for secure attachment of the portable monitoring device to a respective monitored person;
      2) monitoring means to provide for detecting a bodily signal produced by the monitored person;
      3) transmitting means to provide for transmission of a signal;
      4) tamper detection means to provide for detecting tampering with the portable monitoring device attached to the respective monitored person;
      5) receiving means to provide for receiving a distinct signal generated by a detached sending unit;
      6) intervention means to provide for a mechanical intervention to physically dissuade the respective monitored person from a specific course of action;
   b) transmission acquisition means to provide for receiving the signals sent out by each of the portable monitoring devices;
   c) bodily signal reference creation means to provide for creation of a bodily signal reference as detected by the monitoring means; and
   d) storage means to provide for an archival retention within a database of at least a series of bodily signal references of each of the portable monitoring devices of the monitoring system.

2. The monitoring system defined in claim 1 wherein the bodily signal detected by the monitoring means comprises a blood pressure determination.

3. The monitoring system defined in claim 1 wherein the bodily signal detected by the monitoring means comprises a heart beat rate.

4. The monitoring system defined in claim 1 wherein the bodily signal detected by the monitoring means comprises a respiration rate.

5. The monitoring system defined in claim 1 wherein the bodily signal detected by the monitoring means comprises a bodily temperature measurement.

6. The monitoring system defined in claim 1 wherein the bodily signal detected by the monitoring means comprises a blood oxygen level.

7. The monitoring system defined in claim 1 wherein the bodily signal detected by the monitoring means comprises a blood alcohol level.

8. The monitoring system defined in claim 1 wherein each portable monitoring device further comprises receiving means to provide for receiving a distinct signal generated by a detached sending unit; and wherein the monitoring system further comprises positional determining means to provide for generating a position reference indicative of a positional location of each of the portable monitoring devices based upon the distinct signal received by the respective receiving means; and wherein the storage means further provides for an archival retention within the database of at least a series of the position references of each of the portable monitoring devices of the monitoring system.

9. The monitoring system defined in claim 8 wherein the monitoring system further comprises temporal marking means to provide for indicating, within at least a range of temporal references, an associated occurrence reference indicative of when the position reference to the positional location of each of the portable monitoring device occurred, and wherein the storage means further provides for an archival retention within the database of at least a series of the associated occurrence references of each of the portable monitoring devices of the monitoring system.

10. A tracking system to provide for tracking of a plurality of monitored persons, the tracking system comprising:
   a) a portable monitoring device for each of the monitored persons, each portable monitoring device comprising:
      1) securing means to provide for secure attachment of the portable monitoring device to a respective monitored person;
      2) tamper detection means to provide for detecting tampering with the portable monitoring device attached to the respective monitored person;
      3) receiving means to provide for receiving a distinct signal generated by a detached sending unit;
      4) transmitting means to provide for transmission of a signal;
      5) intervention means to provide for a mechanical intervention to physically dissuade the respective monitored person from a specific course of action;
   b) transmission acquisition means to provide for receiving the signals sent out by each of the portable monitoring devices;
   c) positional determining means to provide for generating a position reference indicative of a positional location of each of the portable monitoring devices based upon the distinct signal received by the respective receiving means;
   d) a conditional database having an entry for each portable monitoring device defining rules of conduct for each respective monitored person;
   e) violation comparison means to provide for a comparison of a status of each portable monitoring device indicative of the specific course of action of the respective monitored person against a respective entry within the conditional database to determine if a violation condition exists; and f) intervention activation means to provide for broadcasting a signal for reception by a respective portable monitoring device in response to an indication from the violation comparison means where the respective portable monitoring device activates the intervention means to dissuade the respective monitored person from the specific course of action which was detected by the violation comparison means.

11. The tracking system defined in claim 10 wherein the intervention means further comprises a delivery of a medication.

12. The tracking system defined in claim 10 wherein the intervention means further comprises a delivery of an electrical shock.

13. The tracking system defined in claim 10 further comprising storage means to provide for an archival retention within a database of at least a series of the position references of each of the portable monitoring devices of the tracking system.

14. The tracking system defined in claim 13 wherein the tracking system further comprises temporal marking means to provide for indicating, within at least a range of temporal references, an associated occurrence reference indicative of when the position reference to the positional location of each of the portable monitoring device occurred, and wherein the storage means further provides for an archival retention within the database of at least a series of the associated occurrence references of each of the portable monitoring devices of the tracking system.

15. A dual tracking system to provide for locational tracking of at least one pair of monitored persons, the pair of monitored persons having a restrictee person and a restrictor person, the dual tracking system comprising:

a) a restrictee portable monitoring device for the restrictee person of the pair of monitored persons, the restrictee portable monitoring device comprising:
1) securing means to provide for secure attachment of the restrictee portable monitoring device to the restrictee person;
2) tamper detection means to provide for detection of tampering with the restrictee portable monitoring device attached to the restrictee person;
3) restrictee receiving means to provide for receiving a distinct signal generated by a detached sending unit;
4) restrictee transmitting means to provide for restrictee transmission of a restrictee signal;
5) intervention means to provide for a mechanical intervention to physically dissuade the respective restrictee person from a specific course of action;

b) a restrictor portable monitoring device for the restrictor person of the pair of monitored persons, the restrictor portable monitoring device comprising:

1) transport means to provide for the restrictor person to transport the restrictor portable monitoring device therewith;
2) restrictor receiving means to provide for receiving a distinct signal generated by the detached sending unit;
3) restrictor transmitting means to provide for restrictor transmission of a restrictor signal;

c) transmission acquisition means to provide for receiving the restrictee signal and the restrictor signal;

d) restrictee positional determining means to provide for generating a restrictee position reference indicative of a restrictee positional location of the restrictee portable monitoring device;

e) restrictor positional determining means to provide for generating a restrictor position reference indicative of a restrictor positional location of the restrictor portable monitoring device;

f) comparison means to provide for comparing the restrictee position reference and the restrictor position reference subsequent to the transmission acquisition means receiving the restrictee signal and the restrictor signal;

g) notification means to provide for generating a notification in the event that the restrictee position reference and the restrictor position reference are within a predetermined distance measurement range; and h) intervention activation means to provide for broadcasting a signal for reception by a respective restrictee portable monitoring device in response to an indication from the comparison means where the respective restrictee portable monitoring device activates the intervention means to dissuade the respective restrictee person from the specific course of action which was detected by the comparison means.

16. The dual tracking system defined in claim 15 further comprising storage means to provide for an archival retention within a database of at least a series of the restrictee position references.

17. The dual tracking system defined in claim 16 further comprising temporal marking means to provide for indicating within at least a range of temporal references an associative restrictee occurrence reference indicative of when the restrictee receiving means received the distinct signal; and wherein the storage means further provides for an archival retention within the database of at least a series of the associative restrictee occurrence references.

18. The dual tracking system defined in claim 15 wherein the intervention means further comprises a delivery of a medication.

19. The dual tracking system defined in claim 15 wherein the intervention means further comprises a delivery of an electrical shock.

* * * * *